United States Patent [19]
Bronstein

[11] Patent Number: 5,605,795
[45] Date of Patent: Feb. 25, 1997

[54] ASSAYS USING CHEMILUMINESCENT, ENZYMATICALLY CLEAVABLE SUBSTITUTED 1,2-DIOXETANES AND KITS THEREFOR

[75] Inventor: Irena Y. Bronstein, Newton, Mass.

[73] Assignee: Tropix, Inc., Bedford, Mass.

[21] Appl. No.: 255,795

[22] Filed: Jun. 7, 1994

Related U.S. Application Data

[60] Continuation of Ser. No. 990,800, Dec. 15, 1992, abandoned, which is a division of Ser. No. 574,787, Aug. 30, 1990, Pat. No. 5,112,960, which is a continuation-in-part of Ser. No. 382,125, Jul. 20, 1989, Pat. No. 4,978,614, which is a continuation-in-part of Ser. No. 265,405, Oct. 26, 1988, abandoned, which is a continuation-in-part of Ser. No. 889,823, Jul. 24, 1986.

[51] Int. Cl.$^6$ ............................................. C12Q 1/68
[52] U.S. Cl. ............................................. 435/6
[58] Field of Search ............................ 435/6, 7.1, 8, 12, 435/15, 16, 17, 18, 19, 20, 21, 22, 23, 24, 25, 26, 27, 28, 810; 436/501; 549/212, 220, 221, 222; 935/77, 78

[56] References Cited

U.S. PATENT DOCUMENTS

| | | | |
|---|---|---|---|
| 4,931,223 | 6/1990 | Bronstein et al. | 252/700 |
| 4,950,613 | 8/1990 | Arnold, Jr. et al. | 436/546 |
| 4,952,707 | 8/1990 | Edwards et al. | 549/221 |
| 4,956,477 | 9/1990 | Bronstein et al. | 549/221 |
| 4,959,182 | 9/1990 | Schaap | 252/700 |
| 4,978,614 | 12/1990 | Bronstein et al. | 435/21 |
| 5,013,827 | 5/1991 | Schaap | 536/17.3 |
| 5,068,239 | 11/1991 | Schaap et al. | 548/110 |

(List continued on next page.)

FOREIGN PATENT DOCUMENTS

9000168  11/1990  WIPO .

OTHER PUBLICATIONS

Voyta, et al., *The Journal of Cell Biology*, vol. 109, No. 4, Pt. 2, Oct. 1989.
Edwards, et al. Abstract 272, Book of Abstracts, 198th ACS National Meeting, Sep. 1989.
Edwards, et al., *The Journal of Organic Chemistry*, vol. 55, No. 25, Dec. 7, '90, pp. 6225–6231.

(List continued on next page.)

*Primary Examiner*—W. Gary Jones
*Assistant Examiner*—Ardin H Marschel
*Attorney, Agent, or Firm*—Oblon, Spivak, McClelland, Maier & Neustadt, P.C.

[57] ABSTRACT

Dioxetane compounds reactable with an enzyme to release optically detectable eneregy are disclosed. These compounds have the formula:

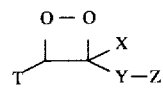

wherein T is a cycloalkyl group or a fused polycycloalkylidene group bonded to the dioxetane ring through a spiro linkage; Y is a fluorescent chromophore capable of absorbing energy to form an excited energy state from which it emits optically detectable energy to return to its original energy state; X is hydrogen or an alkyl, aryl, aralkyl, alkaryl, heteroalkyl, heteroaryl, cycloalkyl or cyclohcteroalkyl group, or an enzyme-cleavable group containing a bond cleavable by an enzyme to yield an electron-rich moiety bonded to the dioxetane ring, Z is hydrogen, hydroxyl or an enzyme-cleavable group containing a bond cleavable by an enzyme to yield an electron-rich moiety bonded to the dioxetane ring, at least one of X and Z being an enzyme-cleavable group, and T also includes a substituent which enhances the solubility of the dioxetane in aqueous solution, or a substituent which facilitates bonding of the dioxetane to a membrane, film, bead, polymer or polymerizable group, or a substituent which enhances the kinetics of the dioxetane enzyme degradation.

63 Claims, 7 Drawing Sheets

U.S. PATENT DOCUMENTS

| | | | |
|---|---|---|---|
| 5,089,630 | 2/1992 | Bronstein et al. | 549/220 |
| 5,094,939 | 3/1992 | Okada et al. | 435/6 |
| 5,145,772 | 9/1992 | Voyta et al. | 435/4 |
| 5,171,534 | 12/1992 | Smith et al. | 422/82.05 |
| 5,177,241 | 1/1993 | Bronstein et al. | 558/194 |
| 5,206,136 | 4/1993 | Monji et al. | 435/5 |
| 5,220,005 | 6/1993 | Bronstein et al. | 536/26.21 |
| 5,223,402 | 6/1993 | Abbas et al. | 435/18 |
| 5,225,584 | 7/1993 | Brooks et al. | 558/189 |
| 5,336,596 | 8/1994 | Bronstein et al. | 435/6 |

OTHER PUBLICATIONS

Bronstein, et al., *Clinical Chemstry*, vol. 37, No. 6, Sep. 1991, 1526–1527.

Martin, et al., *BioTechniques*, vol. 11, No. 1, Jul. 1991, 110–113.

Bronstein, et al. Abstract #1693, *Cell Biology*, Nov. 1989.

Sommer and Tauty, *Nucleic Acids Research*, vol. 17, No. 16, 1989, p. 6749.

ASSAYS USING CHEMILUMINESCENT, ENZYMATICALLY CLEAVABLE SUBSTITUTED 1,2-DIOXETANES AND KITS THEREFOR

This application is a Continuation, of Ser. No. 07/990,800 filed on Dec. 15, 1992, now abandoned, which is a Divisional of Ser. No. 07/574,787, filed Aug. 30, 1990, now U.S. Pat. No. 5,112,960, which is a Continuation-in-Part of Ser. No. 07/382,125, filed Jul. 20, 1989, now U.S. Pat. No. 4,978,614, which is a Continuation-in-Part of Ser. No. 07/265,406, filed Oct. 26, 1988, now abandoned, which is a Continuation-in-Part of Ser. No. 06/889,823, filed Jul. 24, 1986.

FIELD OF THE INVENTION

The invention relates to chemiluminescent, enzymatically cleavable substituted 1,2-dioxetanes, and to their use to detect a substance in a sample.

BACKGROUND OF THE INVENTION

Dioxetanes are compounds having a 4-membered ring in which 2 of the members are adjacent oxygen atoms. Dioxetanes can be thermally or photochemically decomposed to form carbonyl products, e.g., esters, ketones or aldehydes. Release of energy in the form of light (i.e., luminescence) accompanies this decomposition.

SUMMARY OF THE INVENTION

In general, the invention features in a first aspect an improvement in an assay method in which a member of a specific binding pair (i.e., two substances which bind specifically to each other) is detected by means of an optically detectable reaction. The improvement includes the reaction, with an enzyme, of a dioxetane having the formula

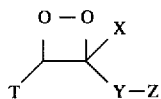

where T is a substituted (i.e., containing one or more $C_1$-$C_7$ alkyl groups or heteroatom groups, e.g., carbonyl groups) or unsubstituted cycloalkyl ring (having between 6 and 12 carbon atoms, inclusive, in the ring) or polycycloalkyl group (having 2 or more fused rings, each ring independently having between 5 and 12 carbon atoms, inclusive), bonded to the 4-membered dioxetane ring by a spiro linkage; Y is a fluorescent chromophore, (i.e., Y is group capable of absorbing energy to form an excited, i.e., higher energy, state, from which it emits light to return to its original energy state); X is hydrogen, a straight or branched chain alkyl group (having between 1 and 7 carbon atoms, inclusive, e.g., methyl), a straight chain or branched heteroalkyl group (having between 1 and 7 carbon atoms, inclusive, e.g., methoxy, hydroxyethyl, or hydroxypropyl), an aryl group (having at least 1 ring, e.g., phenyl), a heteroaryl group (having at least 1 ring, e.g., pyrrolyl or pyrazolyl), a heteroalkyl group (having between 2 and 7 carbon atoms, inclusive, in the ring, e.g., dioxane), an aralkyl group (having at least 1 ring, e.g., benzyl), an alkaryl group (having at least 1 ring, e.g., tolyl), or an enzyme-cleavable group, i.e., a group having a bond which can be cleaved by an enzyme to yield an electron-rich moiety bonded to the dioxetane, e.g., phosphate, where a phosphorus-oxygen bond can be cleaved by an enzyme, e.g., acid phosphatase or alkaline phosphatase, to yield a negatively charged oxygen bonded to the dioxetane; and Z is hydrogen, hydroxyl or an enzyme-cleavable group (as defined above), provided that at least one of X or Z must be an enzyme-cleavable group, so that the enzyme cleaves the enzyme-cleavable group to form a negatively charged substituent (e.g., an oxygen anion) bonded to the dioxetane, the negatively charged substituent causing the dioxetane to decompose to form a luminescent substance (i.e., a substance that emits energy in the form of light) that includes group Y. The luminescent substance is detected as an indication of the presence of the first substance. By measuring the intensity of luminescence, the concentration of the first substance can be determined.

In preferred embodiments, one or more of groups T, X, or Y further include a solubilizing substituent, e.g., a carboxylic acid group;, sulfonic acid group, or their salts, or a quaternary amino salt; group T of the dioxetane is a polycycloalkyl group, preferably adamantyl; the enzyme-cleavable group includes phosphate; and the enzyme includes phosphatase.

The invention also features a kit for detecting a first substance in a sample.

In a second aspect, the invention features a method of detecting an enzyme in a sample. The method involves contacting the sample with the above-described dioxetane in which group Z is capable of being cleaved by the enzyme being detected. The enzyme cleaves group Z to form a negatively charged substituent (e.g., an oxygen anion) bonded to the dioxetane. This substituent destabilizes the dioxetane, thereby causing the dioxetane to decompose to form a luminescent substance that includes group Y of the dioxetane. The luminescent substance is detected as an indication of the presence of the enzyme. By measuring the intensity of luminescence, the concentration of the enzyme can also be determined.

The invention provides a simple, very sensitive method for detecting substances in samples, e.g., biological samples, and is particularly useful for substances present in low concentrations. Because dioxetane decomposition serves as the excitation energy source for chromophore Y, an external excitation energy source, e.g., light, is not necessary. In addition, because the dioxetane molecules are already in the proper oxidation state for decomposition, it is not necessary to add external oxidants, e.g., $H_2O_2$ or $O_2$. Enzyme-activated decomposition allows for high sensitivity because one enzyme molecule can cause many dioxetane molecules to luminesce, thus creating an amplification effect. Moreover, the wavelength (or energy) of emission and the quantum yields of luminescence can be varied according to the choice of the Y substituent of the dioxetane (as used herein, "quantum yield" refers to the number of photons emitted from the luminescent product per number of moles of dioxetane decomposed). In addition, through appropriate modifications of the T, X, and Y groups of the dioxetane, the solubility of the dioxetane and the kinetics of dioxetane decomposition can be varied. The dioxetanes can also be attached to a variety of molecules, e.g., proteins or haptens, or immobilization substrates, e.g., polymer membranes, or included as a side group in a homopolymer or copolymer.

Other features and advantages of the invention will be apparent from the following description of the preferred embodiments thereof, and from the claims.

DESCRIPTION OF THE PREFERRED EMBODIMENTS

Figure 1:
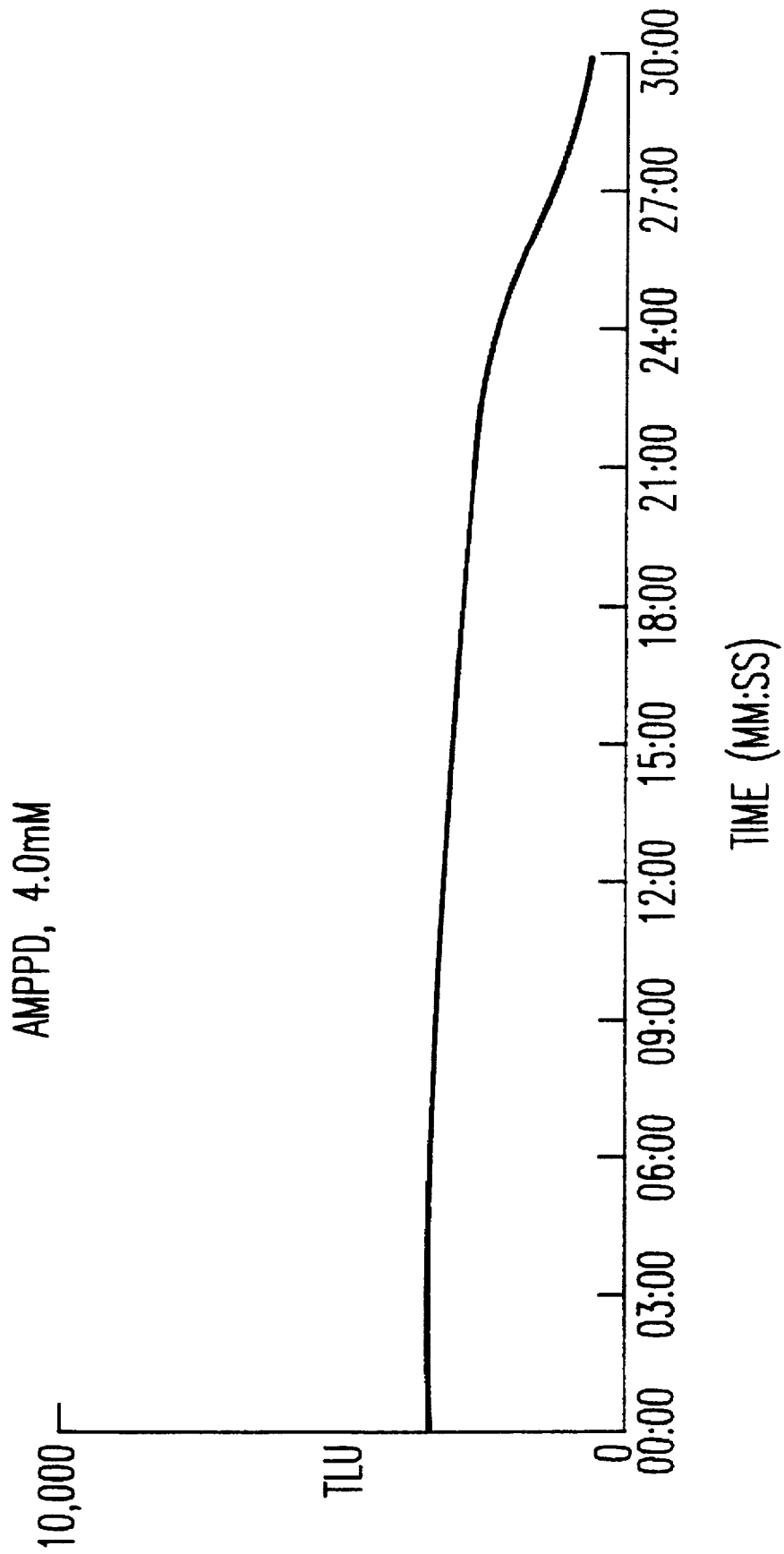
FIGS. 1–3 compare the total luminescence emissions obtained from each of AMPPD and its A-methoxyadamant- 2'-ylidene and B-methoxyadamant-2'-ylidene analogs, respectively, obtained as described in Example IV below.

The structure, synthesis, and use of preferred embodiments of the invention will now be described.

Structure

The invention employs dioxetanes having the structure recited in the Summary of the Invention above. The purpose of group T is to stabilize the dioxetane, i.e., to prevent the dioxetane from decomposing before the enzyme-cleavable group Z is cleaved. Large, bulky, sterically hindered molecules, e.g., fused polycyclic molecules, are the most effective stabilizers. In addition, T preferably contains only C—C and C—H single bonds. The most preferred molecule is an adamantyl group consisting of 3 fused cyclohexyl rings. The adamantyl group is bonded to the 4-membered ring portion of the dioxetane through a spiro linkage.

Group Y is a fluorescent chromophore bonded to enzyme-cleavable group Z. Y becomes luminescent when an enzyme cleaves group Z, thereby creating an electron-rich moiety which destabilizes the dioxetane, causing the dioxetane to decompose. Decomposition produces two individual carbonyl compounds, one of which contains group T, and the other of which contains groups X, Y, and Z; the energy released from dioxetane decomposition causes the Y groups of the latter carbonyl compound to luminesce (if group X is hydrogen, an aldehyde is produced).

The excited state energy of chromophore Y (i.e., the energy chromophore Y must possess in order to emit light) is preferably less than the excited state energy of the ketone containing group T in order to confine luminescence to group Y. For example, when Y is adamantyl, the excited state energy of chromophore Y is preferably less than the excited state energy of spiroadamantane.

Any chromophore Y can be used according to the invention. In general, it is desirable to use a chromophore which maximizes the quantum yield in order to increase sensitivity.

Examples of suitable chromophores include the following:

1) phenyl and phenyl derivatives;
2) naphthalene and naphthalene derivatives, e.g., 5-dimethylaminonaphthalene-1-sulfonic acid and hydroxy naphthalene;
3) anthracene and anthracene derivatives, e.g., 9,10-diphenylanthracene, 9-methylanthracene, 9-anthracene carboxaldehyde, anthryl alcohols and 9-phenylanthracene;
4) rhodamine and rhodamine derivatives, e.g., rhodols, tetramethyl rhodamine, tetraethyl rhodamine, diphenyldimethyl rhodamine, diphenyldiethyl rhodamine, and dinaphthyl rhodamine;
5) fluorescein and fluorescein derivatives, e.g., 5-iodoacetamido fluorescein, 6-iodoacetamido fluorescein, and fluorescein-5-maleimide;
6) eosin and eosin derivatives, e.g., hydroxy eosins, eosin-5-iodoacetamide, and eosin-5-maleimide;
7) coumarin and coumarin derivatives, e.g., 7-dialkylamino-4-methylcoumarin, 4-bromomethyl-7-methoxycoumarin, and 4-bromomethyl-7-hydroxycoumarin;
8) erythrosin and erythrosin derivatives, e.g., hydroxy erythrosins, erythrosin-5-iodoacetamide and erythrosin-5-maleimide;
9) aciridine and aciridine derivatives, e.g., hydroxy aciridines and 9-methyl aciridine;
10) pyrene and pyrene derivatives, e.g., N-(1-pyrene) iodoacetamide, hydroxy pyrenes, and 1-pyrenemethyl iodoacetate;
11) stilbene and stilbene derivatives, e.g., 6,6'-dibromostilbene and hydroxy stilbenes;
12) nitrobenzoxadiazoles and nitrobenzoxadiazole derivatives, e.g., hydroxy nitrobenzoxadiazoles, 4-chloro-7-nitrobenz-2-oxa-1,3-diazole, 2-(7-nitrobenz-2-oxa-1,3-diazol-4-yl-amino)hexanoic acid;
13) quinoline and quinoline derivatives, e.g., 6-hydroxyquinoline and 6-aminoquinoline;
14) acridine and acridine derivatives, e.g., N-methylacridine and N-phenylacridine;
15) acidoacridine and acidoacridine derivatives, e.g., 9-methylacidoacridine and hydroxy-9-methylacidoacridine;
16) carbazole and carbazole derivatives, e.g., N-methylcarbazole and hydroxy-N-methylcarbazole;
17) fluorescent cyanines, e.g., DCM (a laser dye), hydroxy cyanines, 1,6-diphenyl-1,3,5-hexatriene, 1-(4-dimethyl aminophenyl)-6-phenylhexatriene, and the corresponding 1,3-butadienes.
18) carbocyanine and carbocyanine derivatives, e.g., phenylcarbocyanine and hydroxy carbocyanines;
19) pyridinium salts, e.g., 4(4-dialkyldiaminostyryl) N-methyl pyridinium iodate and hydroxy-substituted pyridinium salts;
20) oxonols; and
21) resorofins and hydroxy resorofins.

The most preferred chromophores are hydroxy derivatives of benzene, anthracene or naphthalene; the hydroxy group facilitates bonding to group Z.

Group Z is bonded to chromophore Y through an enzyme-cleavable bond. Contact with the appropriate enzyme cleaves the enzyme-cleavable bond, yielding an electron-rich moiety bonded to a chromophore Y; this moiety initiates the decomposition of the dioxetane into two individual carbonyl compounds e.g., into a ketone or an ester and an aldehyde if group X is hydrogen. Examples of electron-rich moieties include oxygen, sulfur, and amine or amino anions. The most preferred moiety is an oxygen anion. Examples of suitable Z groups, and the enzymes specific to these groups are given below in Table 1; an arrow denotes the enzyme-cleavable bond. The most preferred Z group is a phosphate ester, particularly one bonded to a phenyl chromophore group Y through an oxygen atom, the phenyl group in turn being bonded to the 4-carbon atom of the dioxetane ring, i.e.:

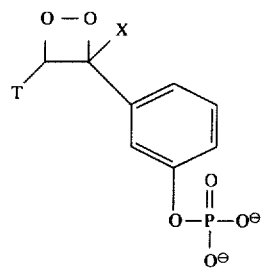

the phosphate ester is cleaved by alkaline or acid phosphatase enzymes.

TABLE 1
| | Group Z | Enzyme |
|---|---|---|
| 1) | 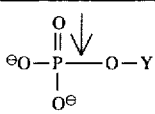 phosphate ester | alkaline and acid phosphatases |
| 2) | 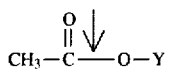 acetate ester | esterases |
| 3) | 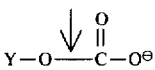 carboxyl | decarboxylases |
| 4) | 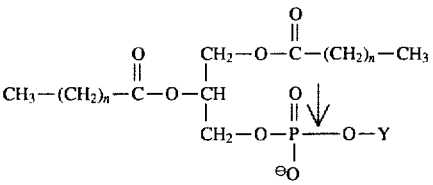 3-phospho-1,2-diacyl glycerides | phospholipase D |
| 5) | 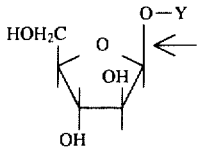 β-D-xyloside | β-xylosidase |
| 6) | 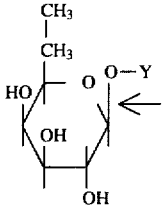 β-D-fucoside | β-D-fucosidase |
| 7) | 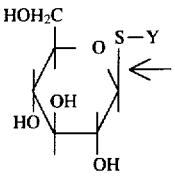 1-thio-D-glucoside | thioglucosidase |
| 8) | 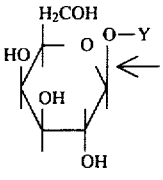 β-D-galactoside | β-D-galactosidase |

TABLE 1-continued
| | Group Z | Enzyme |
|---|---|---|
| 9) | 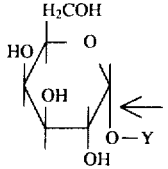<br>α-D-galactoside | α-D-galactosidase |
| 10) | 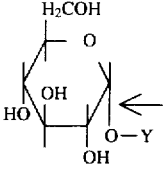<br>α-D-glucoside | α-D-glucosidase |
| 11) | 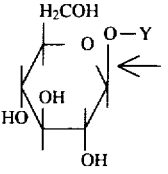<br>β-D-glucoside | β-D-glucosidase |
| 12) | 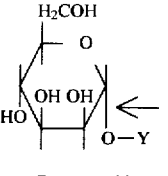<br>α-D-mannoside | α-D-mannosidase |
| 13) | 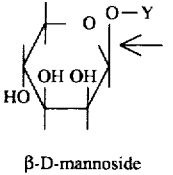<br>β-D-mannoside | β-D-mannosidase |
| 14) | 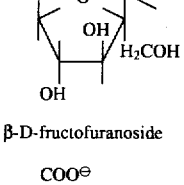<br>β-D-fructofuranoside | β-D-fructofuranosidase |
| 15) | 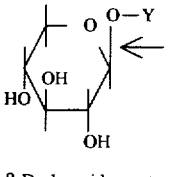<br>β-D-glucosiduronate | β-D-glucosiduronase |

TABLE 1-continued

| | Group Z | Enzyme |
|---|---|---|
| 16) | 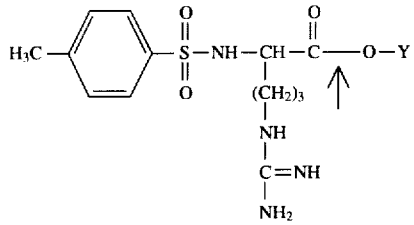 p-toluenesulfonyl-L-arginine ester | trypsin |
| 17) | 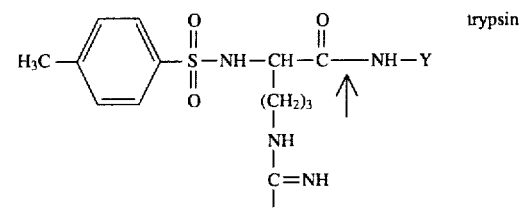 p-toluenesulfonyl-L-arginine amide | trypsin |

Suitable X groups are described in the Summary of the Invention, above. Preferably, X contains one or more solubilizing substituents, i.e., substituents which enhance the solubility of the dioxetane in aqueous solution. Examples of solubilizing substituents include carboxylic acid or carboxylic acid salt groups, e.g., carboxymethyl or carboxyethyl groups, which are most preferred; sulfonic acid or sulfonic acid salt groups, e.g., oxysulfonylmethyl; and quaternary amino salts, e.g., trialkylammonium bromide.

Preferably, the enzyme which cleaves group Z is covalently bonded to a substance having a specific affinity for the substance being detected. Examples of specific affinity substances include antibodies, e.g., anti-hCG; antigens, e.g., hCG, where the substance being detected is an antibody, e.g., anti-hCG; a probe capable of binding to all or a portion of a nucleic acid, e.g., DNA or RNA, being detected; or an enzyme capable of cleaving the Y-Z bond. Bonding is preferably through an amide bond.

Synthesis

In general, the dioxetanes of the invention can be synthesized in any of several ways.

One such synthesis involves first synthesizing an appropriately substituted olefin having the formula:

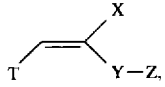

wherein T, Y and Z are as described above. This can be done using the well-known McMurry reaction [see, e.g., McMurry, et al., "Titanium-Induced Reductive Coupling of Carbonyls to Olefins", *J. Org. Chem.*, 43, No. 17 (1978), pp. 3255–3266; *J. Am. Chem. Soc.*, 105 (1983), pp. 1660–1661]. A ketone starting material, T=O, is employed. In this starting material T can be, for example, an adamantyl group that, when spiro bonded through its 2'-carbon atom to the 3-carbon atom of the 1,2-dioxetane, will become the dioxetane's 3-(adamant-2'-ylidene) substituent, or an adamantyl group bearing a substituent that either will be a desired substituent attached to the dioxetane ring's adamantylidene moiety, e.g., a lower alkoxy group such as a methoxy group, or a substituent convertible to a desired substituent by known techniques. For example, 2-substituted-4,5-diphenyloxazoles are known to serve:

... as sources of latent carboxylic acid derivatives which can be readily unmasked by dye sensitized photo oxygenation to produce a reactive triamide which can be hydrolyzed under mild conditions in an aqueous basic medium to the carboxylate salt; See Wasserman, et al., *Tetrahedron*, 37 (1981), pp. 4059–4067.

5-Carboxyadamantan-2-one [see Lantvoev, *Zh. Obshch. Khim.*, 12, 2361–2368 (1976), see also le Noble, et al., *J. Org. Chem.*, 48, 1101–1103 (1983) for a similar preparation of 5-carbomethoxyadamantan-2-one, which can easily be hydrolyzed to the parent carboxylic acid] or 5-carboxymethyladamantan-2-one [see Miura, et al., *Chem. Pharm. Bull.*, 30, 67–73 (1982)] are converted to the corresponding diphenyloxazoles by way of their benzoin or di-p-methoxybenzoin esters. The oxazole group is then converted to the carboxylate after McMurry reaction and phosphorylation as the Z-appended olefin intermediate is reacted with singlet oxygen to give the 1,2-dioxetane simultaneously.

Two equivalents of the ketone starting material T=O, e.g., 5-[2-(4,5-diphenyloxazol-2-yl)methyl]adamantan-2-one, are reacted with one equivalent of an alkyl ester:

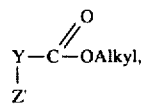

in which Y is, for example, phenyl, Z' is a group Z as described above, e.g., a phosphate ester group bonded through one of its oxygen atoms to the phenyl group (which in turn is bonded to what will become the 4-carbon atom of the 1,2-dioxetane ring), or a group convertible to a group Z by known techniques, e.g., a methoxy group or a phosphorylatable hydroxyl group, and the alkyl group can be a lower alkyl group such as methyl. This reaction takes place using the standard 2:1 ratio of titanium trichloride to lithium aluminum hydride, preferably in the presence of a solvent such as glyme, diglyme, tetrahydrofuran, or the like, along with three equivalents of triethylamine for each mole of titanium trichloride used, at a temperature ranging from about 60° C. to about 90° C. for from about 1 to about 4 hours, following which the reaction mixture preferably is quenched with methanol and worked up under anhydrous conditions.

In those cases in which Z' is a phosphorylatable hydroxyl group-substituted chromophore, e.g., a hydroxyphenyl group, and it is desired to phosphorylate the chromophore's hydroxyl group following the olefin-forming reaction, this can be accomplished using a cyclic acyl phosphate, e.g.:

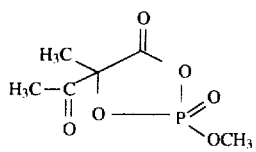

(prepared by reacting 2,2,2-trimethoxy -4,5-dimethyl-1,3-dioxaphospholene with phosgene at 0° C., followed by heating at 120° C. for two hours) and then demethylating this triester with pyridine, which is also present as the solvent, to yield the N-methylpyridinium salt of the cyclic acyl phosphate diester. This salt reacts with the aforementioned hydroxyaryl enol ether as it is added to the same pyridine solution to yield the 3-keto-2-butyloxy phosphate diester of the hydroxyaryl species as its N-methylpyridinium salt. The diester is easily hydrolyzed, with selective loss of the ketobutyloxy group, to the monoester after removing the solvent and stirring the product at room temperature with an aqueous acetonitrile sodium carbonate buffer [see Ramirez, et al., *Angew. Chem. Intn'l. Ed.*, 12, 66–67 (1973), and refs. contd. therein] to give the phosphorylated chromophore.

Appropriately substituted olefins of the formula:

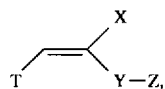

whose T substituent is further substituted with a group or substituent X', which can be a solubilizing substituent which enhances the solubility of the dioxetane in aqueous solution, a substituent which facilitates bonding to, e.g., membranes, films, beads, polymers or polymerizable groups, or a substituent which enhances the kinetics of the dioxetane enzymatic degradation, can also be synthesized by methods such as those disclosed in Edwards U.S. patent application Ser. No. 411,387 (now U.S. Pat. No. 4,956,477) (the "'387 application"), filed Sep. 22, 1989, Edwards, et al. U.S. patent application Ser. No. 402,847, abandoned filed Sep. 6, 1989 (the "'847 application"), Edwards, et al. U.S. patent application Ser. No. 279,176 abandoned (the "'176 application"), filed Sep. 6, 1989, Bronstein, et al. U.S. patent application Ser. No. 07/574,786, now U.S. Pat. No. 5,112,960, filed concurrently herewith (attorney's docket no. 189/300), and Edwards, et al. U.S. patent application Ser. No. 07/574,787 (now U.S. Pat. No. 5,200,005), also filed concurrently herewith (attorney's docket No. 191/289), all of common assignment with this application.

In particular, such olefins can be synthesized in accordance with the methods disclosed in the '847 application by a reaction sequence that can be illustrated schematically as follows, using, for illustrative purposes, the instance in which T is substituted adamantyl or adamant-2'-ylidene ("Ad"), X is methoxy, Y is phenyl, Z is phosphoryloxy and X' is one of the aforementioned solubilizing groups, or a bonding facilitating group, e.g., a carboxylic acid group, or a degradation kinetics enhancing group, e.g., a methoxy group, or a group or substituent readily convertible in known manner to such a group, e.g., a 4,5-diphenyloxazol-2-ylmethoxy group convertible to a carboxylic acid containing group by reaction with $^1O_2$ and subsequent basic hydrolysis.

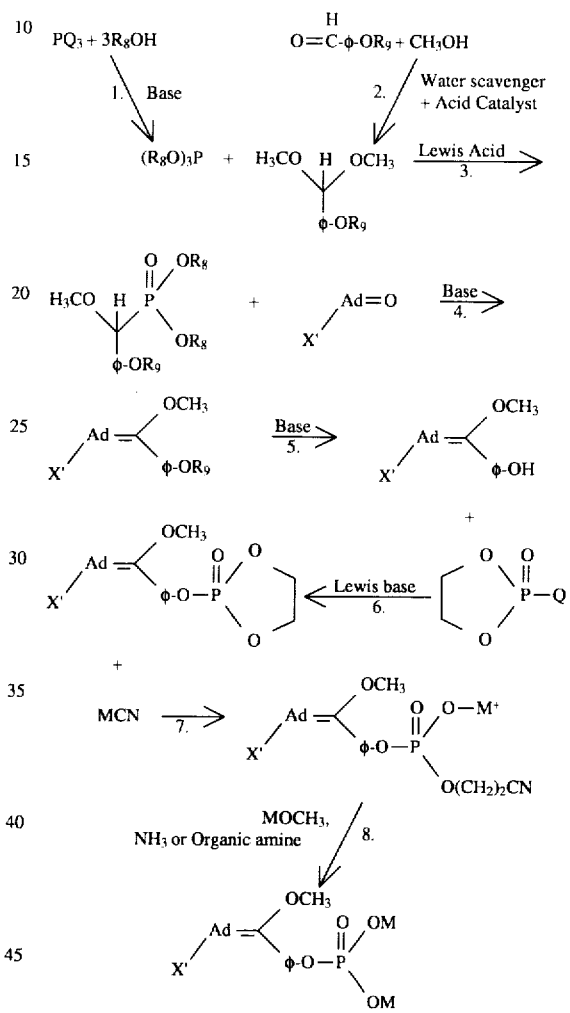

In the foregoing reaction sequence $R_8$ represents a lower alkyl group, e.g., methyl, ethyl or butyl. $R_9$ represents an acyl group containing from 2 to 14 carbon atoms, inclusive, such as acetyl, propionyl, mesitoyl or pivaloyl, Q represents a halogen, e.g., chloro or bromo, or $OR_8$, and M represents, independently, a metal cation, e.g., $Na^+$, or $K^+$, a proton or an ammonium, substituted ammonium, $(H^+)$ pyridinium or quaternary ammonium cation. Thiolate cleavage as described in the '387 application can be used in place of base cleavage of the $OR_9$ group in step 5 of the reaction sequence illustrated above, in which case $R_9$ can be a lower alkyl or aralkyl group, e.g., methyl or benzyl.

The intermediates represented above by the formula:

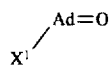

are known compounds, or are readily synthesizable from known starting materials using art-recognized methods.

However, as will be appreciated by those skilled in the art, The X' substituent need not be static during the entire reaction sequence, but may be transformed by reactions which are compatible with other structural considerations at any stage. For example, 5-methoxyadamantan-2-one is prepared as described in Meijer, *Dissertation*, University of Groningen, The Netherlands, 1982. This compound may be used in the Horner Emmons coupling reaction of step 4 in the foregoing reaction sequence to eventually furnish enzyme-cleavable, 5-methoxyadamantylidene substituted, syn- and anti-1,2-dioxetanes. It has been discovered that by starting with 5-bromoadamantan-2-one [Geluk, et al., *Tetrahedron*, 24, 5369 (1968)], the enol ether intermediate produced in step 5 of the sequence (X'=Br) is subject to facile solvolysis in alcohols or liquid ammonia in a bomb at elevated temperature and pressure. The reaction rate of the bromo enol ether phenol with primary, secondary, or tertiary alcohols becomes appreciable only at elevated temperatures (105°–120°) and in the presence of a proton acceptor such as potassium carbonate. In general this reaction is slow, but clean, and avoids the use of silver or heavy metal salts often used to facilitate ether formation. Other halo enol ethers, where X' is chloro or iodo, can also be used in this transformation, but the conditions required for access to the phenolic enol ethers where X' is alkoxy, e.g. methoxy, vary in each case. This reaction can also be applied to heteroaryl substituted alcohols such as 4,5-diphenyl-2-hydroxymethyloxazole [Aldous, et al., *J. Org, Chem.*, 25 pp. 1151–1154 (1960)]. The resulting enol ether, substituted at the 5 position of the adamantane ring with a 4,5-diphenyloxazol-2-ylmethoxy group, can be carried through the synthesis and cleaved during the final step as indicated above.

The second phase in the synthesis of the dioxetanes involves converting the olefin described above to the dioxetane. Preferably, the conversion is effected photochemically by treating by olefin with singlet oxygen ($^1O_2$). $^1O_2$ adds across the double bond to form the dioxetane as follows:

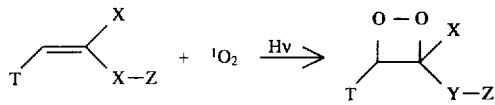

The reaction is carried out in the cold, preferably below about 50° C., in a halogenated solvent, e.g., methylene chloride $^1O_2$ is generated using a photosensitizer. Examples of photosensitizers include poly-bound Rose Bengal (commercially known as Sensitox I and available from Hydron Laboratories, New Brunswick, N.J.), which is preferred, and methylene blue (a well-known dye and pH indicator).

The synthesis of the dioxetane having the formula

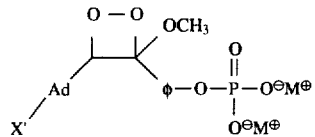

follows:

The olefin having the formula

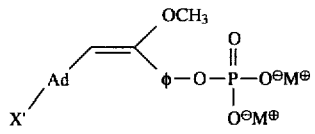

is dissolved in methylene chloride, and the solution is placed in a 2-cm² pyrex tube equipped with a glass paddle; the paddle is driven from above by an attached, glass enclosed, bar magnet. The solution is cooled to 0° C. and 1 g of polymer-bound Rose Bengal is added with stirring. Oxygen is then passed over the surface of the agitated solution while the reaction tube is exposed to light from a 500 W tungsten-halogen lamp (GE Q500 Cl) equipped with a UV-cut off filter (Corning 3060: transmission at 365 nm=0.5%). Thin layer chromatography (tlc) is used to monitor the disappearance of the olefin and the concurrent appearance of the dioxetane. After the reaction is complete (as indicated by tlc), the solvent is removed and the dioxetane is isolated.

Use

A wide variety of assays exist which use visually detectable means to determine the presence or concentration of a particular substance in a sample. The above-described dioxetanes can be used in any of these assays. Examples of such assays include immunoassays to detect antibodies or antigens, e.g., α or β-hCG; enzyme assays; chemical assays to detect, e.g., potassium or sodium ions; and nucleic acid assays to detect, e.g., viruses (e.g., HTLV III or cytomegalovirus, or bacteria (e.g., *E. coli*)).

When the detectable substance is an antibody, antigen, or nucleic acid, the enzyme capable of cleaving group Z of the dioxetane is preferably bonded to a substance having a specific affinity for the detectable substance (i.e., a substance that binds specifically to the detectable substance), e.g., an antigen, an antibody, or a nucleic acid probe. Conventional methods, e.g., carbodiimide coupling, are used to bond the enzyme to the specific affinity substance; bonding is preferably through an amide linkage.

In general, assays are performed as follows. A sample suspected of containing a detectable substance is contacted with a buffered solution containing an enzyme bonded to a substance having a specific affinity for the detectable substance. The resulting solution is incubated to allow the detectable substance to bind to the specific affinity portion of the specific affinity-enzyme compound. Excess specific affinity-enzyme compound is then washed away, and a dioxetane having a group Z that is cleavable by the enzyme portion of the specific affinity-enzyme compound is added. The enzyme cleaves group Z, causing the dioxetane to decompose into two carbonyl compounds (e.g., an ester or ketone); chromophore Y bonded to one of the carbonyl compounds is thus excited and luminesces. Luminescence is detected (using, e.g., a cuvette or camera luminometer), as an indication of the presence of the detectable substance in the sample. Luminescence intensity is measured to determine the concentration of the substance.

When the detectable substance is an enzyme, a specific affinity substance is not necessary. Instead, a dioxetane having a Z group that is cleavable by the enzyme being detected is used. Therefore, an assay for the enzyme involves adding the dioxetane to the enzyme-containing sample, and detecting the resulting luminescence as an indication of the presence and the concentration of the enzyme.

Examples of specific assays follow.

A. Assay for Human IgG

A 96-well microtiter plate is coated with sheep anti-human IgG (F(ab)₂ fragment specific). A serum sample containing human IgG is then added to the wells, and the wells are incubated for 1 hour at room temperature.

Following the incubation period, the serum sample is removed from the wells, and the wells are washed four times, with an aqueous buffer solution containing 0.15M NaCl, 0.01M phosphate, and 0.1% bovine serum albumin (pH 7.4).

Alkaline phosphatase bonded to anti-human IgG is added to each well, and the wells are incubated for 1 hr. The wells are then washed four times with the above buffer solution, and a buffer solution of a phosphate-containing dioxetane of this invention is added. The resulting luminescence caused by enzymatic degradation of the dioxetane is detected in a luminometer, or with photographic film in a camera luminometer.

B. Assay for hCG

Rabbit anti-α-hCG is adsorbed onto a nylon-mesh membrane. A sample solution containing hCG, e.g., urine from a pregnant woman, is blotted through the membrane, after which the membrane is washed with 1 ml of a buffer solution containing 0.15M NaCl, 0.01M phosphate, and 0.1% bovine serum albumin (pH 7.4).

Alkaline phosphatase-labeled anti-β-hCG is added to the membrane, and the membrane is washed again with 2 ml of the above buffer solution. The membrane is then placed in the cuvette of a luminometer or into a camera luminometer, and contacted with a phosphate-containing dioxetane of this invention. The luminescence resulting from enzymatic degradation of the dioxetane is then detected.

C. Assay for Serum Alkaline Phosphatase 2.7 ml of an aqueous buffer solution containing 0.8M 2-methyl-2-aminopropanol is placed in a 12×75 mm pyrex test tube, and 0.1 ml of a serum sample containing alkaline phosphatase added. The solution is then equilibrated to 30° C. 0.2 ml of a phosphate-containing dioxetane of this invention is added, and the test tube immediately placed in a luminometer to record the resulting luminescence. The level of light emission will be proportional to the rate of alkaline phosphatase activity.

D. Nucleic Acid Hybridization Assay

A sample of cerebrospinal fluid (CSF) suspected of containing cytomegalovirus is collected and placed on a membrane, e.g., a nylon or nitrocellulose membrane. The sample is then chemically treated with urea or guanidinium isothiocyanate to break the cell walls and the degrade all cellular components except the viral DNA. The strands of the viral DNA thus produced are separated and attached to the nitrocellulose filter. A DNA probe specific to the viral DNA and labelled with alkaline phosphatase is then applied to the filter; the probe hybridizes with the complementary viral DNA strands. After hybridization, the filter is washed with an aqueous buffer solution containing 0.2M NaCl and 0.1 mM Tris-HCl (pH=8.10) to remove excess probe molecules. A phosphate-containing dioxetane of this invention is added and the resulting luminescence from the enzymatic degradation of the dioxetane is measured in a luminometer or detected with photographic film.

E. Assay for Galactosidase

In the assays described above and in the working examples to follow dioxetanes containing α- or β- galactosidase-cleavable α-D- or β-D-galactoside (galactopyranoside) groups, respectively, can be added, and the luminescence resulting from the enzymatic cleavage of the sugar moiety from the chromophore measured in a luminometer or detected with photographic film.

F. Electrophoresis

Electrophoresis allows one to separate complex mixtures of proteins and nucleic acids according to their molecular size and structure on gel supports in an electrical field. This technique is also applicable to separate fragments of protein after proteolysis, or fragments of nucleic acids after scission by restriction endonucleases (as in DNA sequencing). After electrophoretic resolution of species in the gel, or after transfer of the separated species from a gel to a membrane, the bonds are probed with an enzyme bound to a ligand. For example, peptide fragments are probed with an antibody covalently linked to alkaline phosphatase. For another example, in DNA sequencing alkaline phosphatase—avidin binds to a biotinylated nucleotide base. Thereafter, an AMPPD analog of this invention is added to the gel or membrane filter. After short incubation, light is emitted as the result of enzymatic activation of the dioxetane to form the emitting species. The luminescence is detected by either X-ray or instant photographic film, or scanned by a luminometer. Multichannel analysis further improves the process by allowing one to probe for more than one fragment simultaneously.

G. Solid State Assays

In solid state assays, it is desirable to block nonspecific binding to the matrix by pretreatment of nonspecific binding sites with nonspecific proteins such as bovine serum albumin (BSA) or gelatin. Applicant has determined that some commercial preparations of BSA contain small amounts of substances that exhibit phosphatase activity that will produce undesirable background chemiluminescence from AMPPD. Applicant has also discovered, however, that certain water-soluble synthetic macromolecular substances are efficient blockers of nonspecific binding in solid state assays using dioxetanes. Preferred among such substances are water-soluble polymeric quaternary ammonium salts such as poly(vinylbenzyltrimethylammonium chloride) (TMQ), poly[vinylbenzyl(benzyldimethylammonium chloride)] (BDMQ) or poly[vinylbenzyl(tributylammonium chloride)] (TBQ).

H. Assay for Nucleotidase

An assay for the enzyme ATPase is performed in two steps. In the first step, the enzyme is reacted at its optimal pH (typically pH 7.4) with a substrate comprising ATP covalently linked via a terminal phosphoester bond to a chromophore-substituted 1,2-dioxetane to produce a phosphoryl-chromophore-substituted 1,2-dioxetane. In the second step, the product of the first step is decomposed by the addition of acid to bring the pH to below 6, preferably to pH 2–4, and the resulting light measured in a luminometer or detected with chromatographic film. In a similar two-step procedure, ADPase is assayed using as the substrate an ADP derivative of a chromophore-substituted 1,2-dioxetane of this invention, and 5'-nucleotidase assayed using as the substrate an adenylic acid derivative of a chromophore-substituted 1,2-dioxetane of this invention. The second step can also be carried out by adding the enzyme alkaline phosphatase to decompose the phosphoryl-chromophore-substituted 1,2-dioxetane.

I. Nucleic Acid Sequencing

DNA or RNA fragments, produced in sequencing protocols, can be detected after electrophoretic separation using the chemiluminescent 1,2-dioxetanes of this invention.

DNA sequencing can be performed by a dideoxy chain termination method [Sanger, F., et al., *Proc. Nat. Acad. Sci. (USA)*, 74:5463 (1977)]. Briefly, for each of the four sequencing reactions, single-stranded template DNA is mixed with dideoxynucleotides and biotinylated primer strand DNA. After annealing, Klenow enzyme and deoxyadenosine triphosphate are incubated with each of the four sequencing reaction mixtures, then chase deoxynucleotide triphosphate is added and the incubation continued.

Subsequently, DNA fragments in reaction mixtures are separated by polyacrylamide gel electrophoresis (PAGE). The fragments are transferred to a membrane, preferably a nylon membrane, and the fragments cross-linked to the membrane by exposure to UV light, preferably of short wave length.

After blocking non-specific binding sites with a polymer, e.g., heparin, casein or serum albumin, the DNA fragments on the membrane are contacted with avidin or streptavidin covalently linked to an enzyme specific for the enzyme-cleavable group of the particular 1,2-dioxetane substrates of this invention. As avidin or streptavidin bind avidly to biotin, biotinylated DNA fragments will now be tagged with an enzyme. For example, when the chemiluminscent substrate is disodium 3-(4-methoxyspiro[1,2-dioxetane-3,2'-(5'-methoxy)tricyclo[3.3.1.1$^{3,7}$]decan]-4-yl)phenyl phosphate (methoxy-AMPPD), avidin or streptavidin will be conjugated to a phosphatase. Similarly, when the chemiluminescent substrate is disodium 3-(-4-methoxyspiro[1,2-dioxetane-3,2'-(5'-chloro)tricyclo[3.3.1.1$^{3,7}$]decan]-4-yl)phenyl β-D-galactopyranose (methoxy-AMPGD), avidin or streptavidin are conjugated with β-galactosidase.

Following generation of luminescence by contacting the complex of DNA fragment-biotin-avidin (or streptavidin)-enzyme with the appropriate 1,2-dioxetane at alkaline pH values, e.g., above about pH 8.5, DNA fragments are visualized on light-sensitive film, e.g., X-ray or instant film, or in a photoelectric luminometer instrument.

The detection method outlined above can also be applied to the genomic DNA sequencing protocol of Church, et al. [Church, G. M., et al., *Proc. Nat. Acad. Sci. (USA)*, 81:1991 (1984)]. After transferring chemically cleaved and electrophoretically separated DNA [Maxam, A. M. et al., *Proc. Nat. Acad. Sci. (USA)*, 74:560 (1977)] to a membrane, preferably a nylon membrane, and cross-linking the ladders to the membrane by UV light, specific DNA sequences may be detected by sequential addition of: biotinylated oligonucleotides as hybridization probes; avidin or streptavidin covalently linked to an enzyme specific for an enzyme-cleavable chemiluminescent 1,2-dioxetane of this invention; and, the appropriate 1,2-dioxetane. Images of sequence ladders (produced by PAGE) may be obtained as described above.

Serial reprobing of sequence ladders can be accomplished by first stripping the hybridized probe and chemiluminescent material from a membrane by contacting the membrane with a heated solution of detergent, e.g., from about 0.5 to about 5% sodium dodecylsulfate (SDS) in water at from about 80° C. to about 90° C., cooling to from about 50° C. to about 70° C., hybridizing the now-naked DNA fragments with another biotinylated oligonucleotide probe to generate a different sequence, then generating an imaging chemiluminescence as described above.

Similar visualization methods can be applied to RNA fragments generated by RNA sequencing methods.

Other embodiments are within the following claims.

For example, the enzyme-cleavable group Z can be bonded to group X of the dioxetane, instead of group Y. The specific affinity substance can be bonded to the dioxetane through groups X, Y, or T (preferably group X), instead of the enzyme. In this case, the group to which the specific affinity substance is bonded is provided with, e.g., a carboxylic acid, amino, or maleimide substituent to facilitate bonding.

Groups X, Y or T of the dioxetane can be bonded to a polymerizable group, e.g., a vinyl group, which can be polymerized to form a homopolymer or copolymer.

Groups X, Y, or T of the dioxetane can be bonded to, e.g., membranes, films, beads, or polymers for use in immuno- or nucleic acid assays. The groups are provided with, e.g., carboxylic acid, amino, or maleimide substituents to facilitate bonding.

Groups, X, Y, or T of the dioxetane can contain substituents which enhance the kinetics of the dioxetane enzymatic degradation, e.g., electron-rich moieties (e.g., methoxy).

Groups Y and T of the dioxetane, as well as group-X, can contain solubilizing substituents.

Appropriately substituted dioxetanes can be synthesized chemically, as well as photochemically. For example, the olefin intermediate can be converted to a 1,2-hydroperoxide by reacting the olefin with H$_2$O$_2$ and dibromantin (1,3-dibromo-5,5-dimethyl hydantoin). Treatment of the 1,2-bromohydroperoxide with base, e.g., an alkali or alkaline earth metal hydroxide such as sodium hydroxide or a silver salt, e.g., silver acetate or silver oxide, forms the dioxetane.

The following examples are intended to illustrate the invention in detail, but they are in no way to be taken as limiting, and the present invention is intended to encompass modifications and variations of these examples within the framework of their contents and the claims. All parts and percentages are weight by volume, except TLC solvent mixtures which are volume by volume, or unless otherwise stated.

The $^1$H NMR data given in certain of these examples for enol ether intermediates uses the prime symbol (') to designate aromatic protons, while non-primed numbers refer, in all cases, to substituent adamant-2'-ylidene ring positions, thus:

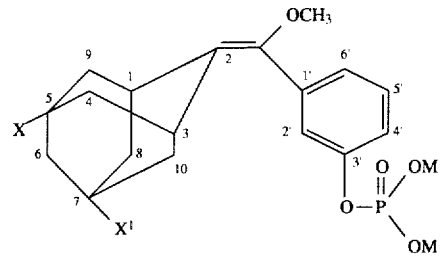

EXAMPLE I

A solution of 2.1 g (0.6 mmol) of 3-(methoxy-5-bromotricyclo[3.3.1.1.$^{3,7}$]dec-2-ylidenemethyl)phenol [prepared as described in Bronstein, et al. U.S. patent application Ser. No. 07/574,786, now U.S. Pat. No. 5,112,960 (attorney's Docket No. 189/300), filed concurrently herewith] in 10 ml of anhydrous methanol, was placed, together with 0.5 g of anhydrous potassium carbonate, in a sealed glass tube. The mixture was heated on an oil bath at 110° C. (105°–120° C. range) for 1.5 days. The contents of the tube were then concentrated on a rotary evaporator, and the residue partitioned between saturated aqueous sodium chloride solution and 20% ethyl acetate in hexanes. The organic fraction was then stripped to furnish 1.56 g (86% yield) of 3-(methoxy-5-methoxytricyclo[3.3.1.1.$^{3,7}$]dec-2-ylidenemethyl)phenol. Column chromatography on silica gel gave an analytical sample as a white solid, m.p. 114°–115° C.

$^1$H NMR (400 MHz, in CDCl$_3$): δ7.2 (1H, dd, J=7.7, 7.6 Hz, H-5'), 6.84 (1H, d, J=7.6 Hz, ArH), 6.73–6.88 (2H, m, ArH), 5.76 (1H, s, Ar OH), 3.44 (1H, br.s, H-1), 3.29 (3H, s, OMe), 3.23 (3H, s, OMe), 2.82 (1H, br.s, H-3), 2.24 (1H, br.s, H-7), 1.57–1.95 (10H, m).

EXAMPLE II

A solution of 0.5 g (1.66 mmol) of 3-(methoxy-5-methoxytricyclo[3.3.1.1.$^{3,7}$]dec-2-ylidenemethyl)phenol in 5 ml of tetrahydrofuran, prepared under argon, was admixed with 0.32 ml (2.33 mmol) of triethylamine and then cooled to 0° C. in an ice bath. 2-Chloro-2-oxo-1,3,2-dioxaphospholane (0.18 ml, 2.0 mmol) was added dropwise with stirring. After 5 minutes the ice bath was removed, and stirring was continued for 45 minutes at room temperature. The reaction mixture was diluted with 20 ml of anhydrous diethyl ether and filtered under argon to exclude moisture. The triethylamine hydrochloride was then washed further with 15 ml of diethyl ether and the filtrate concentrated on the rotary evaporator to give the phosphate triester as a viscous, light orange oil.

The triester, dissolved in 6 ml of molecular sieve-dried dimethylformamide under argon, was reacted for 3.5 hours at room temperature with 98 mg (2.0 mmol) of dry sodium cyanide, added all at once with stirring. The solvent was then removed under vacuum (1.0 mm Hg) with heating to 50° C. A sample of the resulting orange-brown residue, when dissolved in water and subjected to reverse phase analytical chromatography [0.1% sodium bicarbonate (water)—acetonitrile gradient] on a PLRP polystyrene column (Polymer Laboratories), evidenced complete reaction to the intermediate cyanoethyl phosphate diester sodium salt.

The residue was then taken up in 5 ml of methanol and treated dropwise with 0.4 ml of a 4.37M solution (1.66 mmol) of sodium methoxide in methanol, with stirring, for 30 minutes at room temperature. Reverse phase analytical HPLC showed β-elimination to the phosphate monoester to be complete. The solvent was removed and the residue triturated with 5% water/acetone to give a gummy solid. Further trituration with 2% water/acetone gave a hard, off-white solid which was filtered and dried under vacuum (1.0 mm Hg) to give 0.62 g of crude disodium 3-(methoxy-5-methoxytricyclo[3.3.1.1.$^{3,7}$]dec-2-ylidenemethyl) phenyl phosphate, contaminated with inorganic salts.

Reverse phase preparative HPLC [0.1% $NaHCO_3$—water-acetonitrile gradient on a PLRP polystyrene column (Polymer Laboratories)] and lyophilization of the appropriate fractions gave 0.50 g (71%) of purified compound as a white, granular solid.

$^1$HNMR (400 MHz, in $D_2O$: δ 7.16(1H,t,J=7.8 Hz,H-5'), 7.05(1H,d,J=8.1 Hz ,ArH), 6.93(1H,br.s.,H-2'), 6.85(1H, d,J=7.1 Hz, ArH),3.19(4H, s, OMe and H-1),3.06(3H, s, OMe),2.65(1H, br.s., H-3),2.1(1H,br.s.,H-7), 1.29–1.93(10H,m).

EXAMPLE III

A solution of 0.527 g (1.25 mmol) of 3-(methoxy-5-methoxytricyclo[3.3.1.1.$^{3,7}$]dec-2-ylidenemethyl)phenyl phosphate disodium salt in 47 ml of 20% anhydrous methanol in chloroform containing $5.3\times10^{-5}$M methylene blue sensitizing dye in a glass tube was cooled at 5° C. in a water bath and saturated with oxygen by passing a stream of the gas through the solution. While continuing to bubble oxygen through the solution, the tube was irradiated with light from a cooled, 250 watt high pressure sodium lamp while maintaining the temperature at 5° C. A 5 mil thick piece of Kapton polyimide film (du Pont), placed between the sodium vapor lamp and the tube, filtered out unwanted UV radiation. After 10 minutes an equivalent quantity of methylene blue was added and irradiation was continued for an additional 15 minutes.

Analytical HPLC using a water-acetonitrile gradient on a PLRP polystyrene column (Polymer Laboratories) showed two product peaks: an early eluting peak (retention time= 5.95 minutes) and a later eluting peak (retention time=6.45 minutes). The area percent ratio of the early eluting product (A) to the later eluting product (B) was 1.7:1.

The solvent was removed on the rotary evaporator on an ice bath. The residue was dissolved in water (60 ml) containing sodium bicarbonate (200 mg) and filtered through a 0.45 micron nylon membrane. Reverse phase preparative HPLC (water-acetonitrile gradient) allowed separation of the two products. The appropriate fractions were combined and shown to be essentially homogeneous by analytical HPLC. Lyophilization provided 0.191 g of product A and 0.112 g of product B as faintly yellow granular solids. $^1$H NMR confirmed that the products were isomeric syn- and anti-disodium 3-(4-methoxyspiro-[1,2-dioxetane-3,2'-(5'-methoxy)tricyclo[3.3.1.1.$^{3,7}$]-decan]-4-yl)phenyl phosphate. Each isomer produced chemiluminescene upon enzymatic dephosphorylation at pH 10 with alkaline phosphatase, displaying unqiue light vs. time profiles and dramatically reduced noise levels.

$^1$HNMR (400 MHz, $D_2O$, A isomer): δ 6.98–7.41 (4H, m, ArH), 3.08 (3H, s, OMe), 3.01 (3H, s, OMe), 2.97 (1H, br.s, H-1), 2.34 (1H, br.s, H-3), 1.8 (1H, br.s, H-7), 1.36–1.65 (8H, m), 0.99 (1H, d, J=13.2 Hz), 0.78 (1H, d, J=13.1 Hz).

$^1$HNMR (400 MHz, $D_2O$, B isomer): δ 6.97–7.42 (4H, m, ArH), 3.09 (3H, s, OMe), 2.95 (1H, br.s, H-1), 2.93 (3H, s, OMe), 2.32 (1H, br.s, H-3), 1.88 (1H, br.s, H-7), 1.24–1.73 (8H, m), 1.09 (1H, dt, J=12.4, 3.2 Hz), 0.83 (1H, d, J=12.2 Hz).

EXAMPLE IV

A comparison of the total luminescence emission from AMPPD and from the corresponding methoxy adamant-2'-1,2-dioxetanes ylidene (A and B isomers) was made by carrying out total dephosphorylation experiments on each of these compounds.

An aqueous solution of the 1,2-dioxetane (4.0 mM) in 0.05M sodium carbonate/sodium bicarbonate containing 1 mM magnesium chloride was prepared and then equilibrated at 30° C. Ten μl of a 7.64×10M aqueous solution of alkaline phosphatase (calf intestine; Biozyme) was then added, and the chemiluminescence from the resulting solution was recorded using a Turner Model 20E luminometer (Turner Instruments Co.; Sunnyvale, Calif.).

The rates of chemiluminescence decay for each of the three compounds in question, expressed in relative light units (RLU's) per minute, are given in the following table.

TABLE I

| 1,2-Dioxetane | Decay Rate (RLU's) | | | Total Decay |
|---|---|---|---|---|
| | I | II | III | Time (min). |
| AMPPD | 0.1 | 0.3 | 0.8 | 60 |
| Methoxy Adamant-2'--ylidene (A isomer) | 1.6 | — | — | 10 |
| Methoxy Adamant-2'--ylidene (B isomer) | 3.9 | — | — | 8.5 |

Figure 2:
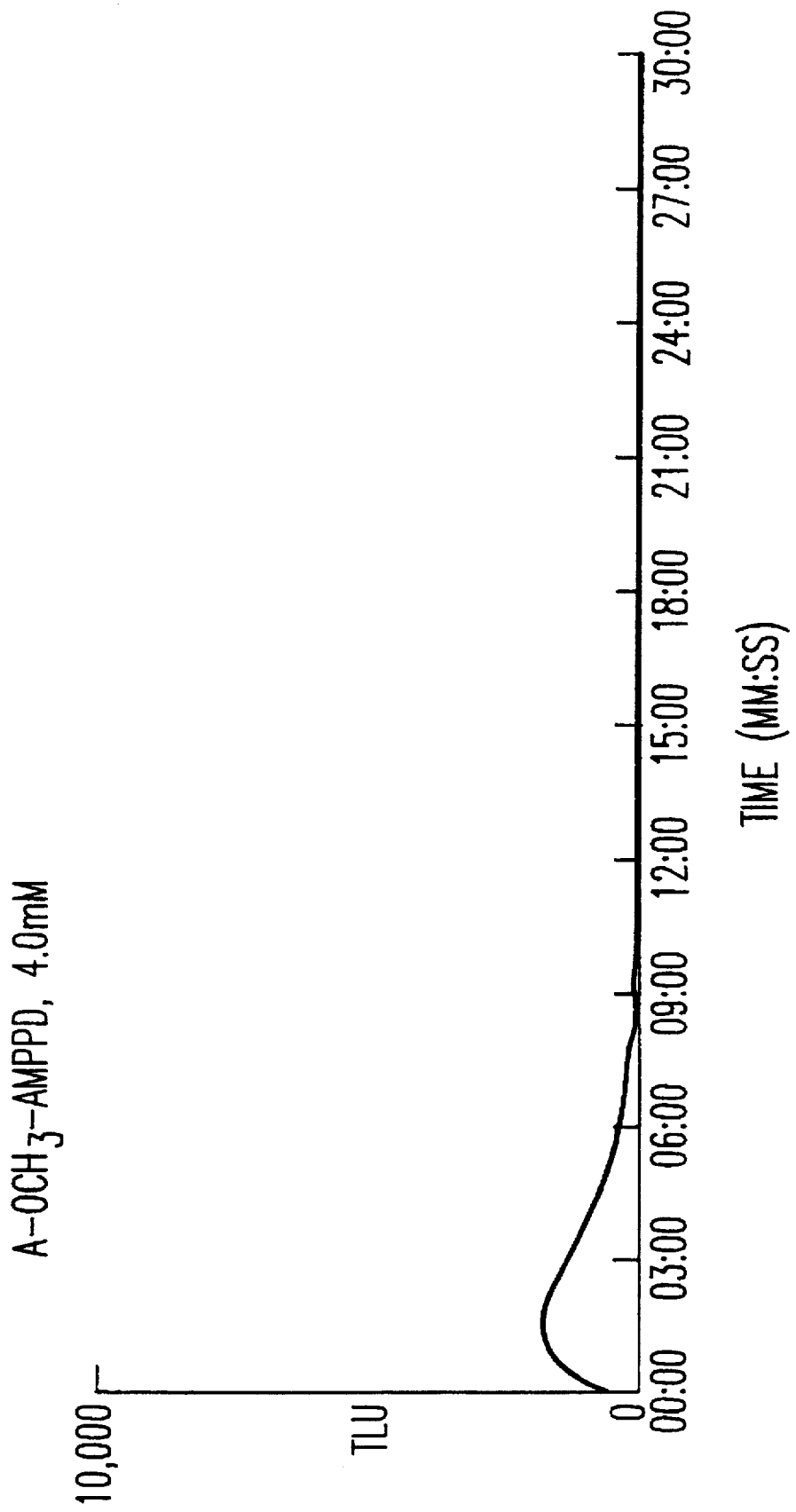
Figure 3:
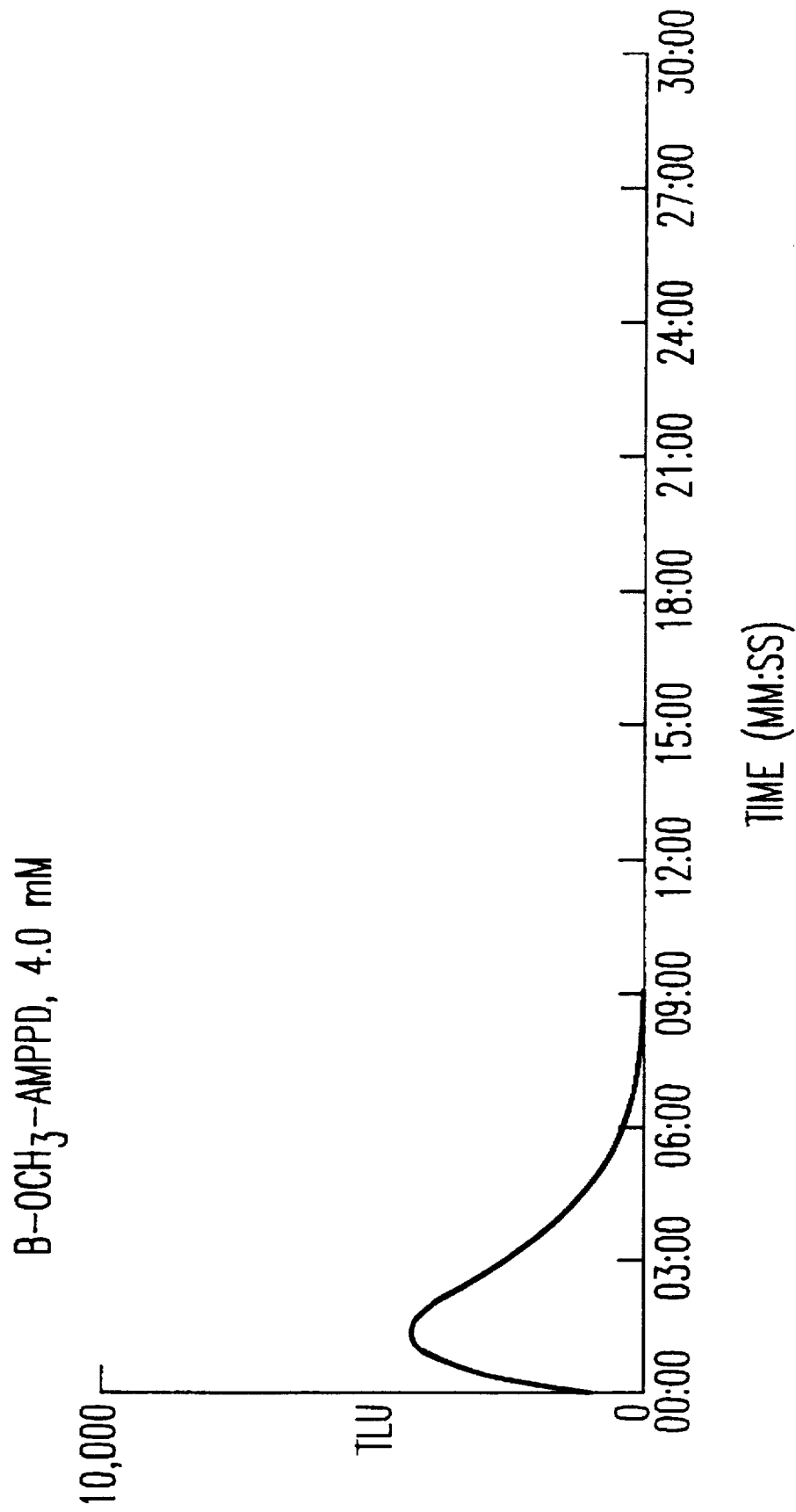

These total chemiluminescence emissions are depicted graphically in FIGS. 1, 2 and 3.

EXAMPLE V

A solution of 1.01 g (2.89 mmol) of 3-(methoxy-5-bromotricyclo[3.3.1.1$^{3,7}$]dec-2-ylidenemethyl)phenol in 6 ml of anhydrous ethanol was placed, with 0.19 g anhydrous potassium carbonate, in a sealed glass tube and heated in an oil bath at 110° C. (105°–120° C. range) for 36 hours. The contents of the tube were then concentrated on a rotary evaporator, and the resulting residue was partitioned between aqueous saturated sodium chloride solution and 20% ethyl acetate in hexanes. The organic fraction was then stripped to give 0.19 g (99% yield) of 3-(methoxy-5-ethoxytricyclo[3.3.1.1.$^{3,7}$]dec-2-ylidenemethyl)phenol as a light yellow gum. Column chromatography on silica gel using an elution gradient of benzene to 10% ethyl acetate in benzene gave an analytical sample as a viscous gum.

$^1$HNMR (400 MHz, in CDCl$_3$): δ7.19(1H,t,J=7.6 Hz, H-5'), 6.83(1H,d,J=7.6 Hz,ArH),6.73–6.8(2H,m,ArH), 5.76(1H,s,ArOH), 3.47(2H,q,J=7 Hz,OC$\underline{H}_2$CH$_3$),3.42(1H, br.s,H-1),3.28(3H,s,OMe),2.8 (1H,br.s,H-3),2.22(1H,br.s,H-7),1.57–1.93(10H,m),1.15(3H,t,J=7 Hz, OCH$_2$C$\underline{H}_3$).

IR (in CHCl$_3$) :3584,3300(OH),2918,2824,1660,1586, 1575, 1448,1294,1168,1090,884 cm$^{-1}$.

EXAMPLE VI

The solvolysis reaction of Example V above was repeated using a number of anhydrous alcohols other than ethanol as solvents. Since the rate of reaction depends on reactant concentrations, reaction temperature, the structure of the alcohol employed, and the solubility of potassium carbonate in the particular alcohol used, the time of reaction varied, depending again on the alcohol chosen. In general, only 6 to 8 hours was required for the reaction with 2-methoxyethanol, due to the fact that the reaction mixture quickly became homogeneous, while 72 hours was necessary for the reaction with n-butanol. Sterically hindered alcohols such as isopropanol and tert-butanol required one week of heating in the oil bath at 110° C. for complete reaction. Spectral data for the products obtained follow.

3-(Methoxy-5-(2-methoxy)ethoxytricyclo [3.3.1.1$^{3,}$
$_7$]dec-2-ylidenemethyl)phenol $^1$HNMR (400 MHz, in CDCl$_3$): δ7.18(1H,t,J=7.6 Hz,H-5'), 6.82(1H,d,J=7.6 Hz,ArH),6.73–6.79(2H,m,ArH), 5.66(1H,s,ArOH), 3.56 (2H,m,OCH$_2$CH$_2$OCH$_3$), 3.5 (2H, m,OCH$_2$CH$_2$OCH$_3$), 3.42 (1H,br.s,H,-1), 3.35(3H,s,OMe), 3.27(3H,s,OMe),2.79(1H,br.s,H-3),2.22 (1H,br.s,H-7), 1.55–1.92(10H,m).

IR (in CHCl$_3$): 3583,3310(OH),2920,2844,1665,1588, 1576,1443,1294,1092,1078,884 cm$^{-1}$.

3-(methoxy-5-butoxytricyclo[3.3.1.1$^{3,7}$]dec-2-ylidenemethyl)phenol $^1$HNMR (400 MHz, in CDCl$_3$): δ7.2(1H,t,J=7.8 Hz,H-5'), 6.84(1H,d,J=7.8 Hz,ArH),6.74–6.8(2H,m,ArH),5.41(1H,s, ArOH), 3.42 (1H,br.s,H-1),3.39 (2H,t,J=6.8 Hz,OCH$_2$CH$_2$CH$_2$CH$_3$),3.28 (1H,s,OMe),2.8(1H,br.s,H-3), 2.22(1H,br.s,H-7),1.58–2.05 (1OH, m ), 1.49 (2H, m, OCH$_2$C$\underline{H}_2$CH$_2$CH$_3$), 1.33 (2H, m, OCH$_2$CH$_2$C$\underline{H}_2$CH$_3$), 0.88(3H, t,J=7.3 Hz,OCH$_2$CH$_2$CH$_2$C$\underline{H}_3$).

IR(in CHCl$_3$): 3584,3310(OH),2924,2845,1664,1588, 1576, 1442,1295,1092,1080,882 cm$^{-1}$.

3-(methoxy-5-isopropoxytricyclo[3.3.1.1$^{3,7}$]dec-2-ylidenemethyl)phenol $^1$HNMR (400 MHz, in CDCl$_3$): δ7.19(1H,t,J=7.7 Hz,H-5'), 6.74–6.88(3H,m,ArH),5.82(1H,s,ArOH),3.95(1H,heptet,J=6.1 Hz), 3.41(1H,br.s,H-1),3.27(3H,s,OMe),2.81(1H, br.s,H-3),2.22(1H, br.s,H-7),1.57–1.93(1OH,m),1.1(6H,d,J= 6.1 Hz,OCH(C$\underline{H}_3$)$_2$).

IR (in CHCl$_3$): 3583,3310(OH),2922,2843,1663,1588, 1575, 1438,1295,1170,1090,990 cm$^{-1}$.

3-(methoxy-5-t-butoxytricyclo[3.3.1.1.$^{3,7}$]dec-2-ylidenemethyl)phenol $^1$HNMR (400 MHz, in CDCl$_3$): δ7.19(1H,t,J=7.8 Hz,H-5'), 6.84(1H,d,J=6.8 Hz,ArH),6.73–6.8(2H,m,ArH), 5.18(1H,s,ArOH), 3.37 (1H,br.s,H-1),3.28(3H,s,OMe), 2.76(1H,br.s,H-3),2.18(1H, br.s,H-7),1.56–2.05(1OH,m), 1.27(9H,s,C(C$\underline{H}_3$)$_3$).

IR (in CHCl$_3$): 3583,3310(OH),2922,2843,1665,1587, 1576,1438,1358,1180,1090,1080,980 cm$^{-1}$.

EXAMPLE VII pBR 322 plasmid (4700 bp) was subjected to a nick translation process using a Trans-Light kit (Tropix, Inc., Bedford, Mass.) to generate a mixture of biotinylated single stranded polynucleotides of 200–2000 bps in length.

This mixture was dotted onto a dry BIODYNE A membrane as three parallel columns of dots of the following concentrations:

| Row of Dots No. | DNA Concentration (picograms) |
| --- | --- |
| 1 | 20.000 |
| 2 | 10.000 |
| 3 | 5.000 |
| 4 | 2.500 |
| 5 | 1.250 |
| 6 | 0.625 |
| 7 | 0.313 |
| 8 | 0.156 |
| 9 | 0.078 |
| 10 | 0.039 |
| 11 | blank[2/] |

[2/]Single stranded DNA, 1 ng.

The membrane was subjected to ultraviolet irradiation (UVP Mineral Light) for 3 minutes to fix the DNA to the surface of the membrane, then air dried. Next, the membrane was blocked in 0.2% casein/0.1% Tween 20 (sorbitan monolaurate polyoxyalkylene) detergent in PBS for 1 hour, following which 1/5000 diluted avidin-alkaline phosphatase conjugate (Tropix, Inc.) in 0.2% casein in PBS was added. The membrane was then incubated for 30 minutes, washed three times (for 5 minutes each time) in 0.2% casein/0.1% Tween 20 detergent in PBS and washed once for five minutes in aqueous 0.1M diethanolamine containing 1 mM magnesium chloride and 0.02% sodium azide, pH 10.0 (substrate buffer).

Next, the three columns of rows of dots 1–5 were individually cut from the membrane ("strips 1–3"), as were the four columns of rows of dots 6–11 ("strips 4–7"). Strips 1–3 were washed with substrate buffer for 30 minutes. Strips 4–7 were blocked in 0.1% BDMQ in substrate buffer for 30 minutes. Both sets of strips were then incubated for 5 minutes in substrate buffer, then individually incubated for five minutes in aqueous solutions (0.25 mM) of 1,2-dioxetanes as indicated below:

| Strip No. | 1,2-Dioxetane |
| --- | --- |
| 1 | AMPPD |
| 2 | Methoxy Adamant-2'-ylidene (A isomer) |
| 3 | Methoxy Adamant-2'-ylidene (B isomer) |
| 4 | AMPPD |
| 5 | Methoxy Adamant-2'-ylidene (A isomer) |
| 6 | Methoxy Adamant-2'-ylidene (B isomer) |
| 7 | Blank |

All strips were then placed in camera luminometers and exposed on Polaroid Type 612 instant black and white film. The improved chemiluminescence intensity obtained using the 3-(substituted adamant-2'-ylidene)1,2-dioxetanes, as compared to AMPPD itself, can be seen by comparing the results shown in Table II below.

1. Protocol for Determining the Sensitivity of the SNAP®/Test for Herpes Simplex Virus I DNA The levels of detection, or the sensitivity, of the SNAP® DNA probe test for Herpes Simplex Virus 1 DNA were determined by performing the test using serially diluted HSVI control plasmid DNA.

TABLE II

ALKALINE PHOSPHATASE-LABELED DNA PROBE DETECTION IN MEMBRANE
WITH AND WITHOUT BDMQ BLOCKING STEP

| Membrane # | Dioxetane | BDMQ Blocking Step | Detection limit 5. min. exp.[1] | (in picograms DNA) 1 min. exp.[2] |
|---|---|---|---|---|
| 1 | AMPPD | no | 2.500 | 5.000 |
| 2 | Methoxy Adamant-2'-ylidene (A isomer) | no | 5.000 | 10.000 |
| 3 | Methoxy Adamant-2'-ylidene (B isomer) | no | 2.500 | 5.000 |
| 4 | AMPPD | BDMQ | 0.625 | 1.250 |
| 5 | Methoxy Adamant-2'-ylidene (A isomer) | BDMQ | 0.625 | 1.250 |
| 6 | Methoxy Adamant-2'-ylidene (B isomer) | BDMQ | .313 | 0.625 |
| 7 | Blank | — | 0 | — |

[1] Five minute exposure was performed 40 minutes after dioxetane addition.
[2] One minute exposure was performed 77 minutes after dioxetane addition.

EXAMPLE VIII

Immunoassays for TSH were conducted on a series of TSH standards using a Hybritech Tandem - E TSH kit (Hybritech, Inc., San Diego, Calif.) according to the manufacturer's instructions included with the kit, except that upon completion of the anti-TSH-alkaline phosphatase conjugate incubation step and wash, the plastic beads were additionally washed with 0.1M diethanolamine, 1 mM magnesium chloride, 0.02% sodium azide buffer, pH 10.0, and then briefly stored in 200 µl of the same buffer.

Chemiluminescent signals from anti-TSH-alkaline phosphatase conjugate bound to the surface of the beads were initiated by adding to the tubes containing beads 300 µl of 0.67 mM buffer solutions containing, respectively, disodium 3-(2'-spiroadamantane)-4-methoxy-4-(3"-phosphoryloxy)phenyl-1,2-dioxetane ("AMPPD"), disodium 3-(4-methoxyspiro-[1,2-dioxetane-3,2'-(5'-methoxy)tricyclo[3.3.1.1$^{3,7}$]decan]-4-yl)phenyl phosphate (A isomer; "A-CH$_3$O-AMPPD") and the corresponding disodium B-isomer ("B-CH$_3$O-AMPPD"), in 0.1M diethanolamine, 1 mM magnesium chloride, 0.02% sodium azide, pH 10.0. The intensity of light emission was subsequently recorded at 7, 13, 19, 25, 31, 40, 50 and 60 minutes after the substrate addition, as a 5 second integral at room temperature (about 25° C.), using a Berthold LB952T Luminometer (Berthold Instrument, Wildbad, Federal Republic of Germany).

Figure 4:
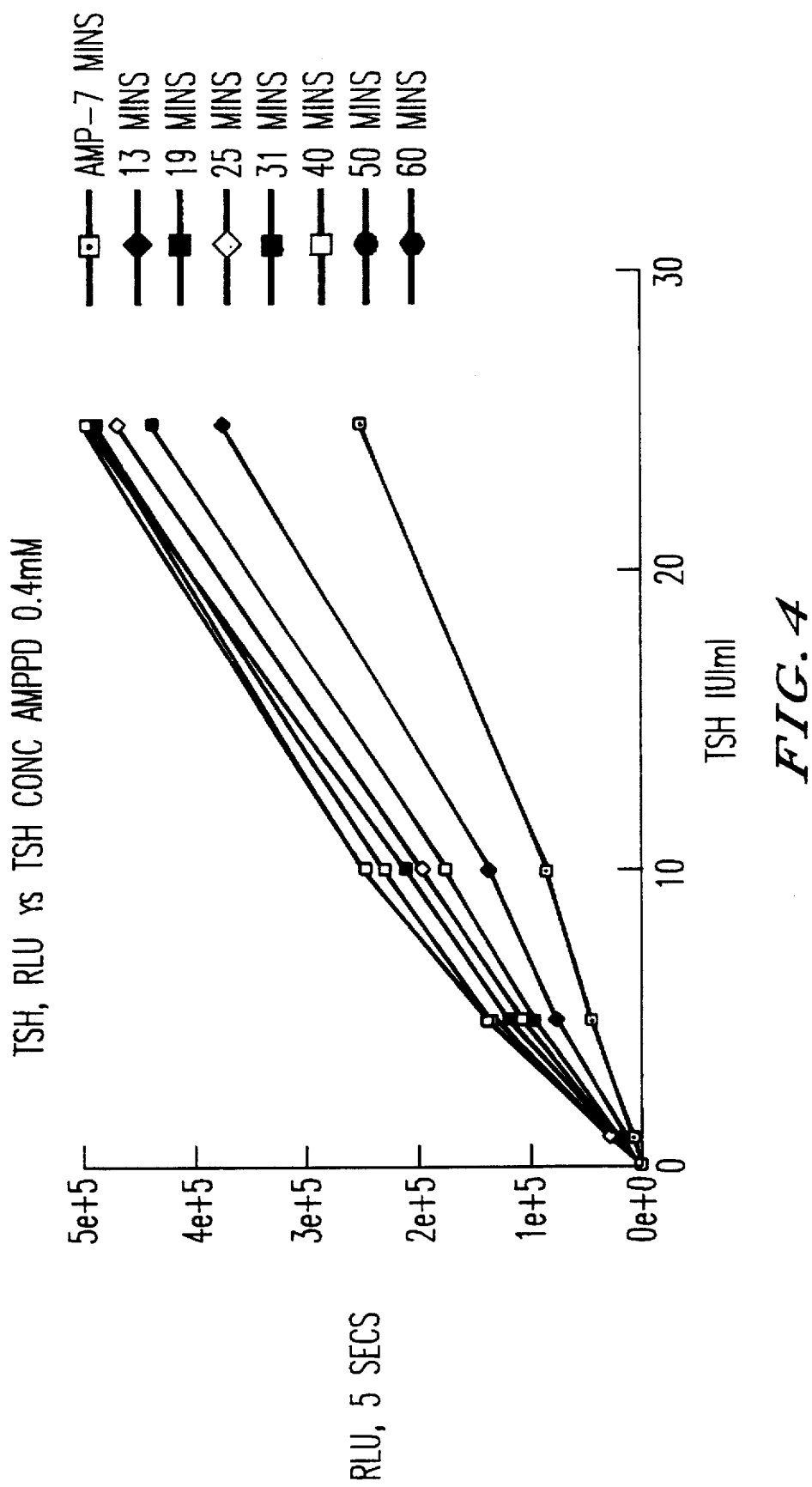
FIGS. 4–6 show TSH, RLU v. TSH for each of AMPPD and its A-methoxyadamant-2'-ylidene and B-methoxyadamant-2'-ylidene analogs, respectively, obtained as described in Example VIII below.
Figure 5:
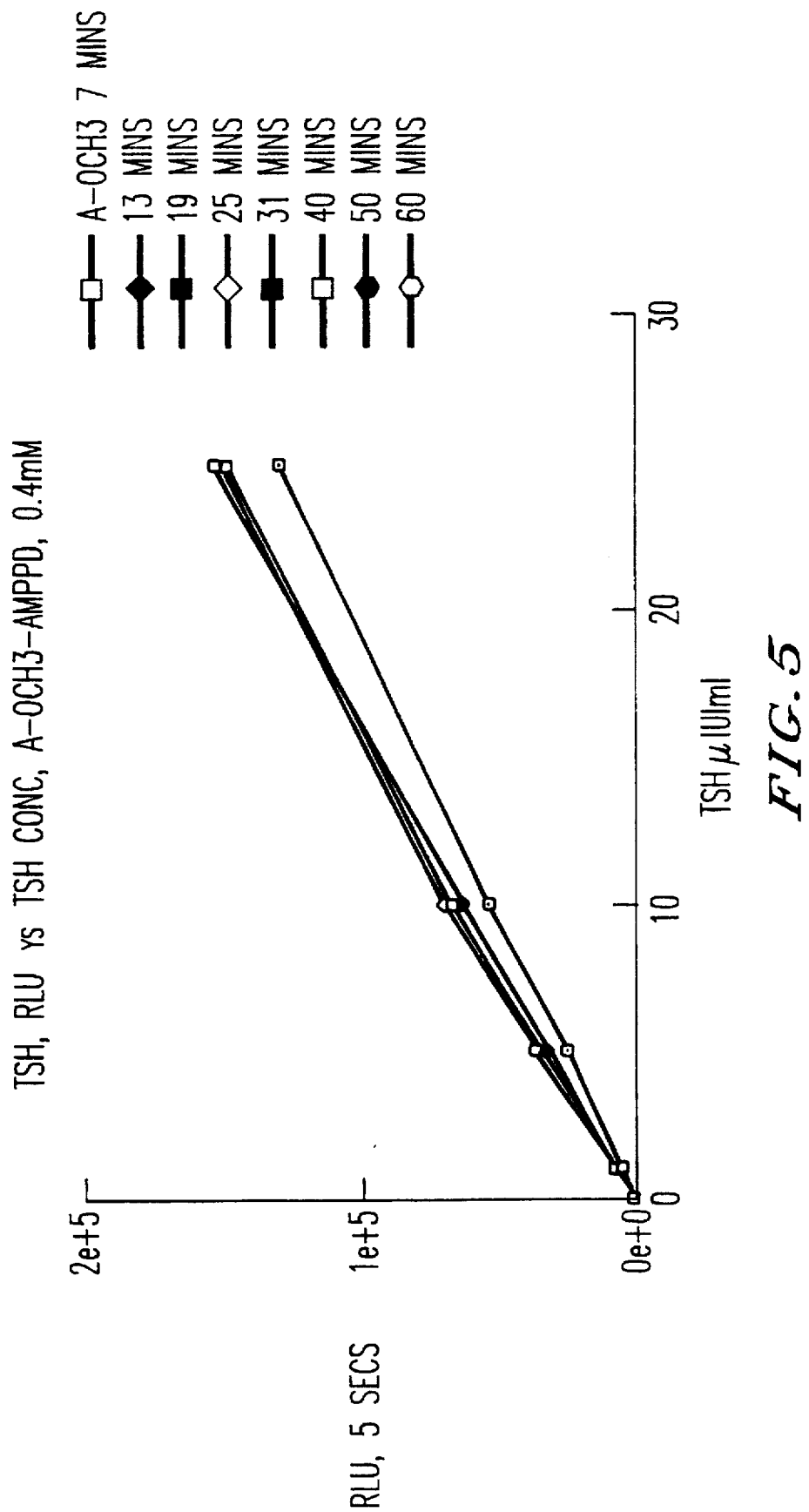
Figure 6:
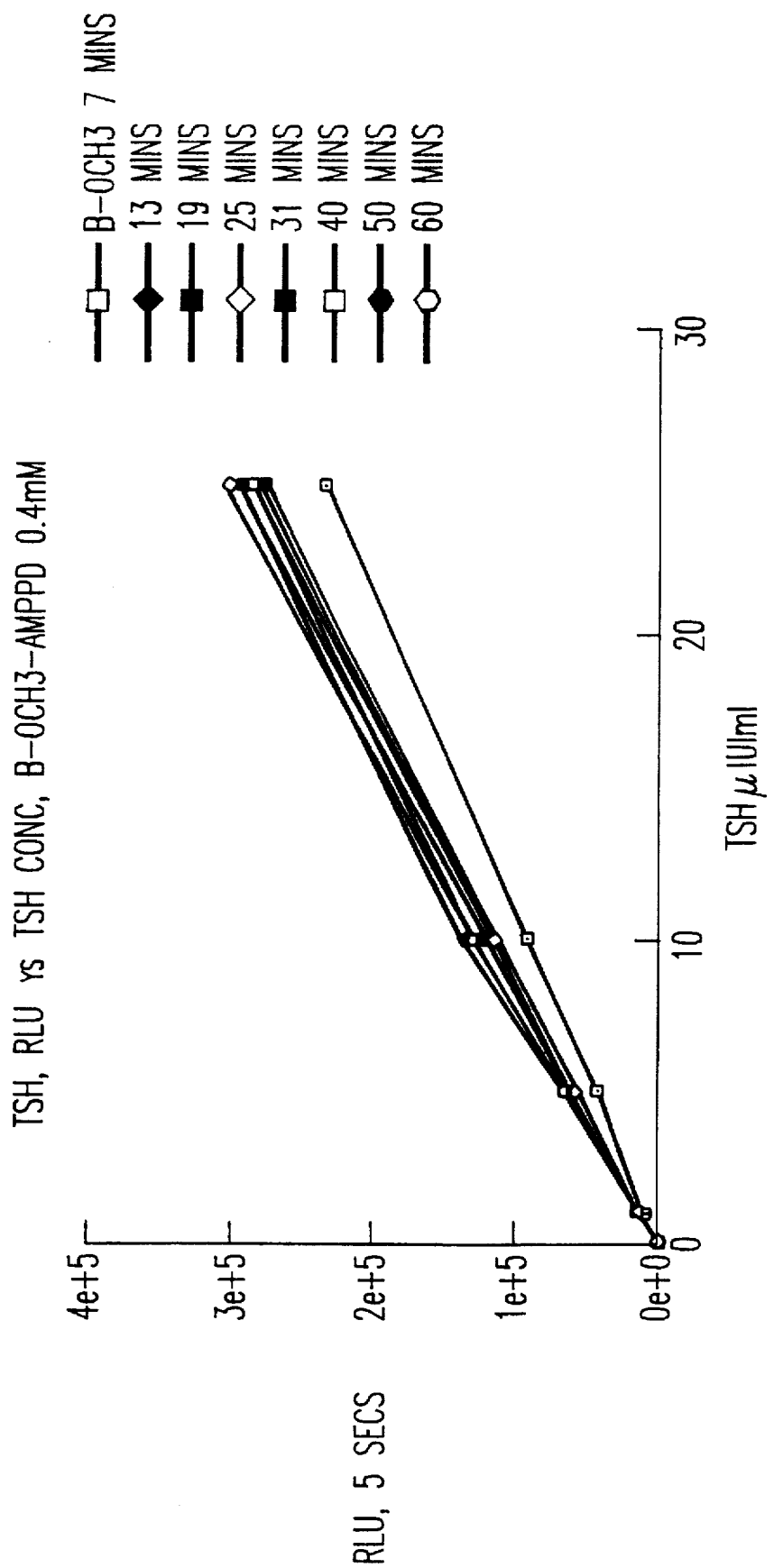

TSH, RLU v. TSH for each of AMPPD, A-CH$_3$O-AMPPD and B-CH$_3$O-AMPPD is shown in FIGS. 4, 5 and 6 respectively.

EXAMPLE IX

The sensitivities of AMPPD and its 5'-A-methoxy analog in the detection of an alkaline phosphate label in Herpes Simplex Virus I DNA by the Snap® probe hybridization assay (E. I. du Pont de Nemours and Co.) were compared in the following manner.

The assay protocol involved the following steps:

a. Preparation of Positive HSVI DNA Plasmic Controls

A stock solution of HSVI plasmid was prepared by dissolving 100 ng (4.8×10$^8$ copies) of the plasmid in 25 µl of sterile, deionized water and serially diluted with 0.3N sodium hydroxide to produce plasmid samples in the concentrations range of 4.88×10$^3$–0.96×10$^8$ copies/µl. The samples were allowed to denature for 15 minutes at room temperature.

b. Preparation of the Membranes, Immobilization of HBV$_c$ Plasmid Control DNA

Gene Screen™ Plus (NEN, DuPont, Boston, Mass.) and Biodyne A (Pall Corp., Glen Cove, N.Y.) membranes were cut into 1×8 cm strips. 1 ul of each dilution of HSVI plasmid sample was spotted on the dry membrane with a pipette tip in contact with the membrane surface to obtain very small, concentrated spots. The membranes were then rinsed with 100 µl of 2M ammonium acetate per spot to neutralize the target immobilized nucleic acid. They were subsequently rinsed with 0.6M sodium chloride, 0.08M sodium citrate, pH 7.0 buffer.

c. Probe Hybridization (i)-Prehybridization

The membranes containing plasmid samples were placed in a heat-sealable pouch in 3 ml of Hybridization Buffer. Prehybridization was carried out for 15 minutes at 55° C.

(ii)-Hybridization

SNAP® alkaline phosphatase labeled probe was reconstituted with 100 ul of the sterile deionized water. The hybridization solution was prepared using 2.5 µl alkaline phosphatase labeled probe solution dissolved in 0.5 ml Hybridization Buffer. Hybridization was performed in a new, heat sealed pouch, with 0.5 ml hybridization solution, for 30 minutes at 55° C. After hybridization, the pouch was opened and the membranes carefully removed and washed with the following buffers:

1. twice with 0.1M sodium chloride, 0.02M sodium citrate, pH 7.0, plus 10 g SDS buffer, for 5 minutes at room temperature,
2. twice with 0.1M sodium chloride, 0.02M sodium citrate, pH 7.0, plus 10 ml Triton X-100 organic synthetic surface-active agent (polyethylene glycol tertoctylphenylether) (Sigma Chemical Co., St. Louis, Mo.), for 5 minutes at 55° C., 3. twice with the above buffer for 5 minutes at room temperature,
4. twice with 0.1M sodium chloride, 0.02M sodium citrate, pH 7.0 buffer for 5 minutes at room temperature,
5. once with 0.1M diethanolamine, 1 mM magnesium chloride, 0.02% sodium azide buffer, at pH 10.0.

Hybridization Buffer was prepared by mixing 250 ml of 3M sodium chloride, 0.4M sodium citrate, pH 7.0, diluted to 800 ml with deionized water, with 5 g Bovine Serum Albumin, 5 g polyvinylpyrrolidione (average MW 40,000) and 10 g SDS, warmed and mixed to dissolve.

d. Chemiluminescent Detection of HSVI Plasmid DNA with AMPPD and $CH_3O$-AMPPD

The hybridized membrane strips were saturated with 7 ml of 0.25 mM 1,2-dioxetane substrate in 0.1M diethanolamine, 1.0 mM magnesium chloride and 0.02% sodium azide at pH 10.0. The membranes were then sealed in a plastic pouch and immediately placed in a camera luminometer where light emission was imaged on Polaroid Instant Black/White 20,000 ASA film, Type 612, for 30 minutes.

2. HSVI Plasmid Dilutions:

| Spot No. | Copies of HSVI DNA per Spot |
| --- | --- |
| 1 | $9.6 \times 10^7$ |
| 2 | $3.2 \times 10^7$ |
| 3 | $1.07 \times 10^7$ |
| 4 | $3.56 \times 10^6$ |
| 5 | $1.19 \times 10^6$ |
| 6 | $3.95 \times 10^5$ |
| 7 | $1.32 \times 10^5$ |
| 8 | $4.39 \times 10^4$ |
| 9 | $1.46 \times 10^4$ |
| 10 | $4.88 \times 10^3$ |

Figure 7A:
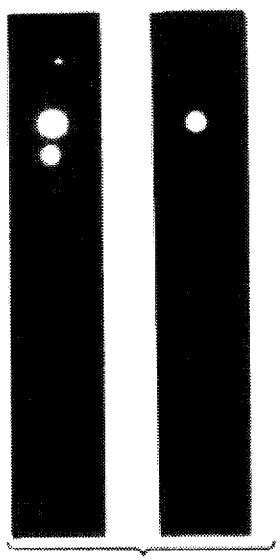
FIGS. 7A and 7B show the sensitivities of AMPPD and its A-methoxyadamant-2'-ylidene analog in the detection of an alkaline phosphate label in Herpes Simplex Virus I DNA by the method described in Example IX below.
Figure 7B:
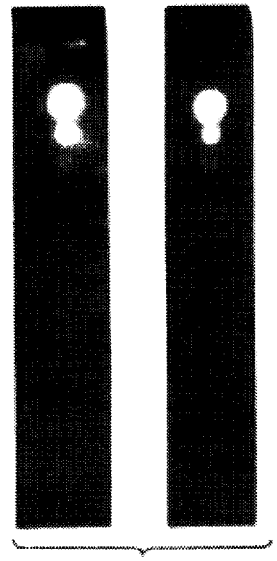

FIG. 7 shows 30 minute images of AMPPD and A-$CH_3O$-AMPPD on the 2 membranes, made using Polaroid Instant 20,000 ASA Black and White film, Type 612.

In FIG. 7, "A" is the images obtained from the Biodyne A membrane strips, "B" is the images obtained from the Gene Screen Plus membrane strips, the (a) strips are AMPPD, and the (b) strips are A-$CH_3O$-AMPPD.

The above discussion of this invention is directed primarily to preferred embodiments and practices thereof. It will be readily apparent to those skilled in the art that further changes and modifications in the actual implementaiton of the concepts described herein can easily be made without departing from the spirit and scope of the invention as defined by the following claims.

What is claimed is:

1. A method of detecting an enzyme in a sample comprising the steps of:
   (a) providing an enzymatically cleavable chemiluminescent 1,2-dioxetane compound capable of producing light energy when decomposed, substantially stable at room temperature before a bond by which an enzymatically cleavable labile substituent thereof is intentionally cleaved, represented by the formula:

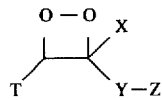

wherein T is a cycloalkyl group or a fused polycycloalkylidene group bonded to the dioxetane ring through a spiro linkage; Y is a fluorescent chromophore capable of absorbing energy to form an excited energy state from which it emits optically detectable energy to return to its original energy state; X is hydrogen or an alkyl, aryl, aralkyl, alkaryl, heteroalkyl, heteroaryl, cycloalkyl or cycloheteroalkyl group, or an enzyme-cleavable group containing a bond cleavable by an enzyme to yield an electron-rich moiety bonded to the dioxetane ring, Z is hydrogen, hydroxyl or an enzyme-cleavable group containing a bond cleavable by an enzyme to yield an electron-rich moiety bonded to the dioxetane ring, at least one of X and Z being an enzyme-cleavable group, and T also includes a substituent which enhances the solubility of the dioxetane in aqueous solution, or a substituent which facilitates bonding of the dioxetane to a membrane, film, bead, polymer or polymerizable group, or a substituent which enhances the kinetics of the dioxetane enzyme degradation (b) contacting said 1,2-dioxetane compound with said sample containing said enzyme; whereupon said enzyme cleaves said enzymatically cleavable labile substituent from said 1,2-dioxetane compound to form a negatively charged substituent bonded to said 1,2-dioxetane compound, said negatively charged substituent causing said 1,2-dioxetane compound to decompose to form a luminescent substance comprising said fluorescent chromophone group; and (c) detecting said luminescent substance as an indication of the presence of said enzyme.

2. A method of claim 1 wherein X is methoxy, Y-Z is a meta phosphate-substituted phenoxy group, and said enzyme is acid or alkaline phosphatase.

3. A method of claim 1 wherein X is methoxy, Y-Z is a meta β-D-galactoside-substituted phenoxy group, and said enzyme is a galactosidase.

4. An assay method for detection of a member of a specific binding pair in a sample by means of an optically detectable reaction, comprising (1) reacting (a) an enzymatically cleavable chemiluminescent 1,2-dioxetane compound capable of producing light energy when decomposed, stable at room temperature before a bond by which an enzymatically cleavable labile substituent thereof is intentionally cleaved, represented by the formula:

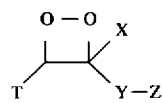

wherein T is carboxylic acid substituted or methoxy substituted adamantyl bonded to the dioxetane ring through a spiro linkage; Y is phenoxy or naphthyloxy; X is methoxy, ethoxy or propoxy, and Z is an enzyme-cleavable group selected from the group consisting of phosphate ester group, acetate ester group, carboxyl group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside, β-D-glucoside group, α-D-mannoside group, β-D-mannoside group, β-D-fructofuranoside group, β-D-glycosiduranate group, p-toluenesulfonyl-L-arginine ester group and a p-toluenesulfonyl-L-arginine amide group with (b) a sample comprising an enzyme bound to one of said specific binding pair if present in said sample, to form a reaction mixture, so that said enzyme cleaves said enzyme-cleavable group to yield an electron-rich moiety bonded to the dioxetane ring to cause the dioxetane to decompose to form a luminescent substance and (2) monitoring said reaction mixture to determine if light is released, wherein the release of light is indicative of the presence of said member of a specific binding pair in said sample.

5. An assay method of claim 4 wherein said specific binding pair comprises an antigen and an antibody.

6. An assay method of claim 4 wherein said specific binding pair comprises an enzyme and a 1,2-dioxetane compound containing a group cleavable by said enzyme.

7. An assay method of claim 6 wherein said enzyme-cleavable group comprises a galactopyranoside, and said enzyme comprises a galactosidase.

8. An assay method of claim 4, conducted using a solid matrix, wherein nonspecific binding to said matrix is blocked by pretreating said matrix with a polymeric quaternary ammonium salt.

9. An assay method of claim 4, carried out in the further presence of a water-soluble enhancing substance that increases specific light energy production above that produced in its absence.

10. An assay method of claim 9, wherein said water-soluble enchancing substance is serum albumin.

11. An assay method of claim 9, wherein said enhancing substance is a polymeric quaternary ammonium salt.

12. An assay method of claim 11, wherein said polymeric quaternary ammonium salt is poly(vinylbenzyltrimethylammonium chloride), poly[vinylbenzyl(benzyldimethylammonium chloride)] or poly[vinylbenzyl(tributylammonium chloride)].

13. An assay method of claim 9, wherein said enhancing substance comprises a positively charged polymeric quaternary ammonium salt and fluorescein capable of forming a ternary complex with the negatively charged substituent of said 1,2-dioxetane compound produced following enzyme-catalyzed decomposition of said 1,2-dioxetane compound, whereby energy transfer occurs between said negatively charged substituent and fluorescein and light energy is emitted by fluorescein.

14. An assay method of claim 12, wherein said polymeric quaternary ammonium salt is poly(vinylbenzyltrimethylammonium chloride), poly[vinylbenzyl(benzyldimethylammonium chloride)] or poly[vinylbenzyl(tributylammonium chloride)].

15. A hybridization assay method for detection of the presence of a nucleic acid selected from the group consisting of DNA, RNA and fragments thereof in a sample, comprising:

1) contacting nucleic acid in the sample with a labeled complementary oligonucleotide probe to form a hybridized pair, 2) contacting the hybridized pair with a molecule which binds strongly to the label of the oligonucleotide, said strongly binding molecule being conjugated with an enzyme capable of cleaving an enzymatically-cleavable 1,2-dioxetane to release light energy, 3) adding to said conjugated, hybridized pair an enzymatically cleavable 1,2-dioxetane substrate represented by the formula

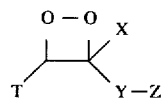

wherein T is carboxylic acid substituted or methoxy substituted adamantyl bonded to the dioxetane ring through a spiro linkage; Y is phenoxy or naphthyloxy; X is methoxy, ethoxy or propoxy, and Z is an enzyme-cleavable group selected from the group consisting of phosphate ester group, acetate ester group, carboxyl group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside, β-D-glucoside group, α-D-mannoside group, β-D-mannoside group, β-D-fructofuranoside group, β-D-glycosiduranate group, p-toluenesulfonyl-L-arginine ester group and a p-toluenesulfonyl-L-arginine amide group; to form a reaction mixture 4) monitoring said reaction mixture to detect the production of light wherein light production is indicative of the presence of said nucleic acid in said sample.

16. The hybridization assay method of claim 15, wherein said oligonucleotide probe binds to all of said nucleic acid.

17. The hybridization assay method of claim 15, wherein said oligonucleotide probe binds to a portion of said nucleic acid.

18. The assay method of claim 15, wherein the label of said oligonucleotide probe is biotin.

19. An assay method of claim 15 wherein the molecule capable of strong interaction with the label of the oligonucleotide is avidin or streptavidin.

20. An assay method of claim 15 wherein the enzyme is an acid or alkaline phosphatase, X is methoxy, and Y-Z is a meta phosphate-substituted phenoxy group.

21. An assay method of claim 13 wherein the enzyme is a galactosidase, X is methoxy, and Y-Z is a meta β-D-galactoside-substituted phenoxy group.

22. An assay method of claim 15 wherein light energy is detected by light-sensitive film.

23. An assay method of claim 15 wherein light energy is detected by a photoelectric cell.

24. An assay method of claim 15 wherein said oligonucleotide probe is covalently labeled with an enzyme capable of decomposing said 1,2-dioxetane to emit light energy.

25. An assay method of claim 15 wherein said label on said oligonucleotide probe comprises a covalently bound antigen that is immunochemically bound to an antibody-enzyme conjugate, wherein said antibody is directed to said antigen and said enzyme is capable of decomposing said 1,2-dioxetane compound to emit light energy.

26. An assay method of either claim 24 or 25 wherein said enzyme is an acid or alkaline phosphatase, X is methoxy, and Y-Z is a meta phosphate-substituted phenoxy group.

27. An assay method of either claim 24 or 25 wherein said enzyme is a galactosidase, X is methoxy, and Y-Z is a meta β-D-galactoside-substituted phenoxy group.

28. An assay method of any one of claims 24 or 25 wherein the binding of said probe to said nucleic acid is carried out on a nylon membrane.

29. A kit for detecting a first substance in a sample, comprising (1) an enzymatically cleavable chemiluminescent 1,2-dioxetane compound capable of producing light energy when decomposed, stable at room temperature before a bond by which an enzymatically cleavable labile substituent thereof is intentionally cleaved, represented by the formula:

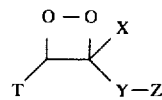

wherein T is carboxylic acid substituted or methoxy substituted adamantyl bonded to the dioxetane ring through a spiro linkage; Y is phenoxy or naphthyloxy; X is methoxy, ethoxy or propoxy, and Z is an enzyme-cleavable group selected from the group consisting of phosphate ester group, acetate ester group, carboxyl group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside, β-D-glucoside group, α-D-mannoside group, β-D-mannoside group, β-D-fructofuranoside group, β-D-glycosiduranate group, p-toluenesulfonyl-L-arginine ester group and a p-toluenesulfonyl-L-arginine amide group; and (2) an enzyme capable of cleaving said enzyme cleavable group.

30. The kit of claim 29, wherein X is methoxy, Y-Z is a meta phosphate-substituted phenoxy group, and said enzyme is acid or alkaline phosphatase.

31. The kit of claim 29, wherein X is methoxy, Y-Z is a β-D-galactoside-substituted phenoxy group, and said enzyme is a galactosidase.

32. The kit of any one of claims 29, inclusive, further comprising image-reproducing means for detecting said light energy.

33. The kit of claim 32, wherein said image-reproducing means is photographic film.

34. A kit for detecting a nucleic acid or fragment thereof in a sample by hybridization of said nucleic acid or fragment to a complementary labeled oligonucleotide probe, comprising (1) an enzymatically cleavable chemiluminescent 1,2-dioxetane compound capable of producing light energy when decomposed, stable at room temperature before a bond by which an enzymatically cleavable labile substituent thereof is intentionally cleaved, represented by the formula:

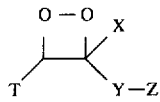

wherein T is carboxylic acid substituted or methoxy substituted adamantyl bonded to the dioxetane ring through a spiro linkage; Y is phenoxy or naphthyloxy; X is methoxy, ethoxy or propoxy, and Z is an enzyme-cleavable group selected from the group consisting of phosphate ester group, acetate ester group, carboxyl group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside, β-D-glucoside group, α-D-mannoside group, β-D-mannoside group, β-D-fructofuranoside group, β-D-glycosiduranate group, p-toluenesulfonyl-L-arginine ester group and a p-toluenesulfonyl-L-arginine amide group; (2) a covalently enzyme-labeled oligonucleotide probe wherein said enzyme cleaves said enzyme-cleavable group; and, (3) a nylon membrane.

35. The kit of claim 34 wherein X is methoxy, Y-Z is a meta phosphate-substituted phenoxy group, and said enzyme is acid or alkaline phosphatase.

36. The kit of claim 34 wherein X is methoxy, Y-Z is a meta β-D-galactoside-substituted phenoxy group, and said enzyme is a galactosidase.

37. The kit of claim 34, further comprising image-reproducing means for detecting said light energy.

38. The kit of claim 37 wherein said image-reproducing means is photographic film.

39. A kit for detecting a nucleic acid or fragment thereof in a sample by hybridization of said nucleic acid or fragment to a complementary labeled oligonucleotide probe, comprising (1) an enzymatically cleavable chemiluminescent 1,2-dioxetane compound capable of producing light energy when decomposed, substantially stable at room temperature before a bond by which an enzymatically cleavable labile substituent thereof is intentionally cleaved, represented by the formula:

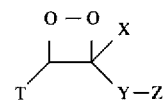

wherein T is carboxylic acid substituted or methoxy substituted adamantyl bonded to the dioxetane ring through a spiro linkage; Y is phenoxy or naphthyloxy; X is methoxy, ethoxy or propoxy, and Z is an enzyme-cleavable group selected from the group consisting of phosphate ester group, acetate ester group, carboxyl group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside, β-D-glucoside group, α-D-mannoside group, β-D-mannoside group, β-D-fructofuranoside group, β-D-glycosiduranate group, p-toluenesulfonyl-L-arginine ester group and a p-toluenesulfonyl-L-arginine amide group; (2) a complementary oligonucleotide probe covalently labeled with biotin or a biotin derivative; avidin or streptavidin covalently bound to an enzyme which cleaves said enzyme-cleavable group; and, (3) a nylon membrane.

40. The kit of claim 39 wherein X is methoxy, Y-Z is a meta phosphate-substituted phenoxy group, and said enzyme is acid or alkaline phosphatase.

41. The kit of claim 39, wherein X is methoxy, Y-Z is a meta β-D-galactoside-substituted phenoxy group, and said enzyme is a galactosidase.

42. The kit of 39, further comprising image-reproducing means for detecting said light energy.

43. The kit of claim 42 wherein said image-reproducing means is photographic film.

44. A kit for detecting a nucleic acid or fragment thereof in a sample by hybridization of said nucleic acid or fragment to a complementary labeled oligonucleotide probe, comprising (1) an enzymatically cleavable chemiluminescent 1,2-dioxetane compound capable of producing light energy when decomposed, stable at room temperature before a bond by which an enzymatically cleavable labile substituent thereof is intentionally cleaved, represented by the formula:

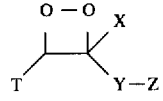

wherein T is carboxylic acid substituted or methoxy substituted adamantyl bonded to the dioxetane ring through a spiro linkage; Y is phenoxy or naphthyloxy; X is methoxy, ethoxy or propoxy, and Z is an enzyme-cleavable group selected from the group consisting of phosphate ester group, acetate ester group, carboxyl group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside, β-D-glucoside group, α-D-mannoside group, β-D-mannoside group, β-D-fructofuranoside group, β-D-glycosiduranate group, p-toluenesulfonyl-L-arginine ester group and a p-toluenesulfonyl-L-arginine amide group; (2) a complementary oligonucleotide probe covalently labeled with an antigen; (3) an antibody directed to said antigen covalently bound to an enzyme which cleaves said enzyme-cleavable group; and, (4) a nylon membrane.

45. The kit of claim 44 wherein said enzyme is an acid or alkaline phosphatase, X is methoxy, and Y-Z is a meta phosphate-substituted phenoxy group.

46. The kit of claim 44 wherein said enzyme is a galactosidase, X is methoxy, and Y-Z is a meta β-D-galactoside-substituted phenoxy group.

47. The kit of claim 44, further comprising image-reproducing means for detecting said light energy.

48. The kit of claim 47 wherein said image-reproducing means is photographic film.

49. The kit of any one of claims 29, 34, 39, 44, further comprising a water-soluble enhancing substance that increases specific light energy production above that produced in its absence.

50. The kit of claim 49 wherein said water-soluble enhancing substance is serum albumin.

51. The kit of claim 49 wherein said enhancing substance is a polymeric quaternary ammonium salt.

52. The kit of claim 51 wherein said polymeric quaternary ammonium salt is poly(vinylbenzyltrimethylammonium chloride), poly[vinylbenzyl(benzyldimethylammonium chloride)] or poly[vinylbenzyl(tributylammonium chloride)].

53. The kit of claim 49 wherein said enhancing substance comprises a positively charged polymeric quaternary ammonium salt and fluorescein capable of forming a ternary complex with the negatively charged product of said 1,2-dioxetane compound produced following enzyme-catalyzed decomposition of said 1,2-dioxetane compound, whereby energy transfer occurs between said negatively charged product and fluorescein and light energy is emitted by fluorescein.

54. The kit of claim 53 wherein said polymeric quaternary ammonium salt is poly(vinylbenzyltrimethylammonium chloride), poly[vinylbenzyl(benzyldimethylammonium chloride)] or poly[vinylbenzyl(tributylammonium chloride)].

55. A kit for detecting a protein in a sample, comprising an enzymatically cleavable chemiluminescent 1,2-dioxetane compound capable of producing light energy when decomposed, substantially stable at room temperature before a bond by which an enzymatically cleavable labile substituent thereof is intentionally cleaved, represented by the formula:

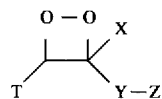

wherein T is a cycloalkyl group or a fused polycycloalkylidene group bonded to the dioxetane ring through a spiro linkage; Y is a fluorescent chromophore capable of absorbing energy to form an excited energy state from which it emits optically detectable energy to return to its original energy state; X is hydrogen or an alkyl, aryl, aralkyl, alkaryl, heteroalkyl, heteroaryl, cycloalkyl or cycloheteroalkyl group, or an enzyme-cleavable group containing a bond cleavable by an enzyme to yield an electron-rich moiety bonded to the dioxetane ring, Z is hydrogen, hydroxyl or an enzyme-cleavable group containing a bond cleavable by an enzyme to yield an electron-rich moiety bonded to the dioxetane ring, at least one of X and Z being an enzyme-cleavable group, and T also includes a substituent which enhances the solubility of the dioxetane in aqueous solution, or a substituent which facilitates bonding of the dioxetane to a membrane, film, bead, polymer or polymerizable group, or a substituent which enhances the kinetics of the dioxetane enzyme degradation; an antibody directed to said protein covalently bound to an enzyme capable of decomposing said 1,2-dioxetane compound to emit light energy; and, a membrane upon which protein-antibody binding is conducted.

56. The kit of claim 55 wherein said membrane is a nylon or nitrocellulose membrane.

57. The kit of claim 55 wherein X is methoxy, Y-Z is a meta phosphonate-substituted phenoxy group, and said enzyme is acid or alkaline phosphatase.

58. The kit of claim 55 wherein X is methoxy, Y-Z is a meta β-D-galactoside-substituted phenoxy group, and said enzyme is a galactosidase.

59. The kit of any one of claims 55–58 inclusive, further comprising image-reproducing means for detecting said light energy.

60. The kit of claim 59 wherein said image reproducing means is photographic film.

61. A kit for detecting a protein in a sample comprising an enzymatically cleavable chemiluminescent 1,2-dioxetane compound capable of producing light energy when decomposed, substantially stable at room temperature before a bond by which an enzymatically cleavable labile substituent thereof is intentionally cleaved, represented by the formula:

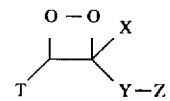

wherein T is a cycloalkyl group or a fused polycycloalkylidene group bonded to the dioxetane ring through a spiro linkage; Y is a fluorescent chromophore capable of absorbing energy to form an excited energy state from which it emits optically detectable energy to return to its original energy state; X is hydrogen or an alkyl, aryl, aralkyl, alkaryl, heteroalkyl, heteroaryl, cycloalkyl or cycloheteroalkyl group, or an enzyme-cleavable group containing a bond cleavable by an enzyme to yield an electron-rich moiety bonded to the dioxetane ring, Z is hydrogen, hydroxyl or an enzyme-cleavable group containing a bond cleavable by an enzyme to yield an electron-rich moiety bonded to the dioxetane ring, at least one of X and Z being an enzyme-cleavable group, and T also includes a substituent which enhances the solubility of the dioxetane in aqueous solution, or a substituent which facilitates bonding of the dioxetane to a membrane, film, bead, polymer or polymerizable group, or a substituent which enhances the kinetics of the dioxetane enzyme degradation; a first antibody directed to said protein; and, a second antibody directed to said first antibody covalently bound to an enzyme capable of decomposing said 1,2-dioxetane compound.

62. The kit of claim 61 wherein X is methoxy, Y-Z is a meta phosphate-substituted phenoxy group, and said enzyme is acid or alkaline phosphatase.

63. The kit of claim 61 wherein X is methoxy, Y-Z is a meta β-D-galactoside-substituted phenoxy group, and said enzyme is a galactosidase.

* * * * *

UNITED STATES PATENT AND TRADEMARK OFFICE
CERTIFICATE OF CORRECTION

PATENT NO. : 5,605,795
DATED : February 25, 1997
INVENTOR(S) : Irena Y. BRONSTEIN It is certified that error appears in the above-indentified patent and that said Letters Patent is hereby corrected as shown below:

On the title page, Item [60] and the top of Column 1, the Related U.S. Application Data should read:

--Continuation of Ser. No. 990,800, Dec. 15, 1992, abandoned, which is a division of Ser. No. 574,787, Aug. 30, 1990, Pat. No. 5,220,005, which is a continuation-in-part of Ser. No. 382,125, Jul.20, 1989, Pat. No. 4,978, 614, which is a continuation-in-part of Ser. No. 265,406, Oct. 26, 1988, abandoned, which is a continuation-in-part Ser. No. 889,823, Jul. 24, 1986.--

Signed and Sealed this

Seventeenth Day of June, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,605,795

DATED : February 25, 1997

INVENTOR(S) : Irena Y. Bronstein

It is certified that error appears in the above-identified patent and that said Letters Patent is hereby corrected as shown below:

Cover Page, Abstract, Line 2, "eneregy" should read -- energy --.
On drawing
Sheet 4, Figure 4, in the figure title, "RLU ys TSH" should read -- RLU vs TSH --; on the scale for the X axis, "TSH IUIml" should read -- TSH, $\mu$IU/ml --.
Drawing
Sheet 5, Figure 5, in the figure title, "RLU ys TSH" should read -- RLU vs TSH --; on the scale for the X axis, "TSH $\mu$IUIml" should read -- TSH, $\mu$IU/ml --.
Drawing
Sheet 6, Figure 6, in the figure title, "RLU ys TSH" should read -- RLU vs TSH --; on the scale for the X axis, "TSH $\mu$IUIml" should read -- TSH, $\mu$IU/ml --.

Column 18, lines 51 and 63 "...tricyclo[3.3.1.1$^{3,7}$]dec-" should read -- ...tricyclo[3.3.1.1$^{3,7}$]dec- --.

Column 19, lines 30 and 46 "...tricyclo[3.3.1.1$^{3,7}$]dec-" should read -- ...tricyclo[3.3.1.1$^{3,7}$]dec- --.

UNITED STATES PATENT AND TRADEMARK OFFICE
CERTIFICATE OF CORRECTION

PATENT NO. : 5,605,795
DATED : February 25, 1997
INVENTOR(S) : Irena Y. Bronstein It is certified that error appears in the above-identified patent and that said Letters Patent is hereby corrected as shown below:

Column 20, line 10 "...tricyclo[3.3.1.1.$^{3,7}$]-decan]" should read --...tricyclo[3.3.1.1$^{3,7}$]-decan] --.

Column 21, line 2 "ytricyclo[3.3.1.1.$^{3,7}$]dec-" should read -- ytricyclo[3.3.1.1$^{3,7}$]dec- --.

Column 22, line 1 "...tricyclo[3.3.1.1.$^{3,7}$]dec-" should read --...tricyclo[3.3.1.1$^{3,7}$]dec- --.

Signed and Sealed this

Nineteenth Day of May, 1998

*Attest:*

BRUCE LEHMAN

*Attesting Officer*   Commissioner of Patents and Trademarks